US012746121B2

(12) United States Patent
Keogh et al.

(10) Patent No.: US 12,746,121 B2
(45) **Date of Patent: *Sep. 29, 2026**

(54) TRANS-SEPTAL DELIVERY SYSTEM AND METHODS OF USE

(71) Applicant: Medtronic, Inc., Minneapolis, MN (US)

(72) Inventors: James Keogh, Maplewood, MN (US); Joshua Dwork, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 739 days.

This patent is subject to a terminal disclaimer.

(21) Appl. No.: 18/188,451

(22) Filed: Mar. 22, 2023

(65) Prior Publication Data

US 2023/0218396 A1 Jul. 13, 2023

Related U.S. Application Data

(63) Continuation of application No. 16/807,010, filed on Mar. 2, 2020, now Pat. No. 11,612,482.

(Continued)

(51) Int. Cl.
*A61F 2/24* (2006.01)
*A61F 2/966* (2013.01)

(52) U.S. Cl.
CPC .......... *A61F 2/2436* (2013.01); *A61F 2/2418* (2013.01); *A61F 2/2466* (2013.01); *A61F 2/9661* (2020.05); *A61F 2220/0016* (2013.01)

(58) Field of Classification Search
CPC ............................. A61F 2/2436; A61F 2/9661
See application file for complete search history.

(56) References Cited

U.S. PATENT DOCUMENTS 7,621,948 B2 11/2009 Herrmann et al.
8,105,375 B2 1/2012 Navia et al.

(Continued)

FOREIGN PATENT DOCUMENTS

WO 2011057087 A1 5/2011
WO 2011137531 A1 11/2011

(Continued)

OTHER PUBLICATIONS

International Search Report, Application No. PCT/US2020/020858, dated Jun. 19, 2020.

(Continued)

*Primary Examiner* — Alvin J Stewart
(74) *Attorney, Agent, or Firm* — Medler Ferro Woodhouse & Mills PLLC

(57) ABSTRACT

A delivery system for delivering a heart valve prosthesis includes a heart valve prosthesis and a delivery catheter. The heart valve prosthesis includes an anchoring member and an inner valve support, and further includes a radially collapsed configuration and a radially expanded configuration. The delivery catheter includes a handle, an outer shaft, an intermediate shaft, an inner shaft, and a distal tip component. The delivery catheter further includes a delivery configuration. In the delivery configuration, the outer shaft of the delivery catheter is configured to retain a first portion of the anchoring member, the intermediate shaft is configured to retain a first portion of the inner valve support, and the distal tip component is configured to retain a second end of the anchoring member and a second end of the inner valve support each in a radially compressed state.

13 Claims, 19 Drawing Sheets

Related U.S. Application Data

(60) Provisional application No. 62/814,815, filed on Mar. 6, 2019.

(56) References Cited

U.S. PATENT DOCUMENTS

| | | | | |
|---|---|---|---|---|
| 8,591,460 | B2 | 11/2013 | Wilson et al. | |
| 9,078,994 | B2 | 7/2015 | Rosenman et al. | |
| 9,125,740 | B2 * | 9/2015 | Morriss | A61F 2/2445 |
| 9,345,573 | B2 | 5/2016 | Nyuli et al. | |
| 9,750,607 | B2 * | 9/2017 | Ganesan | A61F 2/2439 |
| 10,213,301 | B2 * | 2/2019 | Ganesan | A61B 90/57 |
| 10,449,039 | B2 * | 10/2019 | Ganesan | A61F 2/2409 |
| 10,702,378 | B2 * | 7/2020 | Miyashiro | A61F 2/243 |
| 10,751,173 | B2 * | 8/2020 | Morriss | A61F 2/2466 |
| 10,806,574 | B2 * | 10/2020 | Lally | A61F 2/2412 |
| 10,945,835 | B2 * | 3/2021 | Morriss | A61F 2/2409 |
| 11,612,482 | B2 * | 3/2023 | Keogh | A61F 2/2418 623/2.11 |
| 11,684,474 | B2 * | 6/2023 | Srinimukesh | A61F 2/2439 623/2.11 |
| 12,336,909 | B2 * | 6/2025 | Gupte | A61F 2/2436 |
| 2003/0036791 | A1 | 2/2003 | Philipp et al. | |
| 2004/0260394 | A1 | 12/2004 | Douk et al. | |
| 2008/0082166 | A1 * | 4/2008 | Styrc | A61F 2/2418 623/2.18 |
| 2010/0049313 | A1 | 2/2010 | Alon et al. | |
| 2011/0015616 | A1 | 1/2011 | Straubinger et al. | |
| 2011/0208297 | A1 | 8/2011 | Tuval et al. | |
| 2012/0022633 | A1 | 1/2012 | Olson et al. | |
| 2012/0059458 | A1 | 3/2012 | Buchbinder et al. | |
| 2013/0060328 | A1 | 3/2013 | Rothstein | |
| 2013/0226290 | A1 | 8/2013 | Yellin et al. | |
| 2013/0231735 | A1 | 9/2013 | Deem et al. | |
| 2013/0274870 | A1 * | 10/2013 | Lombardi | A61F 2/2427 623/2.11 |
| 2013/0310928 | A1 | 11/2013 | Morriss et al. | |
| 2014/0039611 | A1 | 2/2014 | Lane et al. | |
| 2014/0350669 | A1 | 11/2014 | Gillespie et al. | |
| 2014/0371844 | A1 * | 12/2014 | Dale | A61F 2/2436 623/2.11 |
| 2014/0379074 | A1 | 12/2014 | Spence et al. | |
| 2015/0119981 | A1 | 4/2015 | Khairkhahan et al. | |
| 2015/0173897 | A1 | 6/2015 | Raanani et al. | |
| 2015/0238315 | A1 | 8/2015 | Rabito et al. | |
| 2015/0272731 | A1 | 10/2015 | Racchini et al. | |
| 2015/0297346 | A1 | 10/2015 | Duffy et al. | |
| 2016/0051362 | A1 | 2/2016 | Cooper et al. | |
| 2017/0035569 | A1 | 2/2017 | Deem et al. | |
| 2017/0128205 | A1 * | 5/2017 | Tamir | A61F 2/2436 |
| 2017/0319342 | A1 | 11/2017 | Duffy et al. | |
| 2018/0021129 | A1 | 1/2018 | Peterson et al. | |
| 2018/0055629 | A1 | 3/2018 | Oba et al. | |
| 2018/0296339 | A1 * | 10/2018 | McLean | A61F 2/2436 |
| 2018/0344457 | A1 | 12/2018 | Gross et al. | |
| 2019/0008640 | A1 | 1/2019 | Cooper et al. | |
| 2019/0151086 | A1 * | 5/2019 | Lally | A61F 2/2418 |
| 2019/0175375 | A1 * | 6/2019 | Schreck | A61F 2/2436 |
| 2021/0369451 | A1 * | 12/2021 | Mcveigh | A61F 2/2436 |
| 2022/0280297 | A1 * | 9/2022 | Zhang | A61F 2/2418 |
| 2024/0299163 | A1 * | 9/2024 | Scheinblum | A61F 2/2418 |
| 2024/0315842 | A1 * | 9/2024 | Zhang | A61F 2/2436 |
| 2024/0398558 | A1 * | 12/2024 | Tuval | A61F 2/24 |
| 2025/0205051 | A1 * | 6/2025 | Cobar | A61F 2/2436 |

FOREIGN PATENT DOCUMENTS

| | | | | |
|---|---|---|---|---|
| WO | 2012177942 A1 | | 12/2012 | |
| WO | 2013177684 A1 | | 12/2013 | |
| WO | 2014121275 A1 | | 8/2014 | |
| WO | 2014181336 A1 | | 11/2014 | |
| WO | WO-2018005779 A1 | * | 1/2018 | A61F 2/2436 |

OTHER PUBLICATIONS

Opposition filed in EP Application No. 20714445.2, Jun. 24, 2026, 86 pages.

* cited by examiner

TRANS-SEPTAL DELIVERY SYSTEM AND METHODS OF USE

CROSS-REFERENCE TO RELATED APPLICATIONS

This application is a continuation of U.S. patent application Ser. No. 16/807,010, filed Mar. 2, 2020, which claims the benefit of U.S. Provisional Application No. 62/814,815, filed Mar. 6, 2019, the contents of both of which are incorporated by reference herein in their entirety.

FIELD OF THE INVENTION

The present invention relates to systems and methods of deploying a heart valve prosthesis at the site of a native valve. More particularly, the present invention relates to a delivery system for trans-septally delivering a heart valve prosthesis within an annulus of a native heart valve.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream direction.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate. Valvular stenosis may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a low-profile or compressed/contracted configuration so that the heart valve prosthesis can be advanced through the patient's vasculature. Once positioned at the treatment site, the heart valve prosthesis can be expanded to engage tissue at the diseased native heart valve region to, for instance, hold the heart valve prosthesis in position. While these heart valve prostheses offer minimally invasive methods for heart valve repair and/or replacement, challenges remain to providing effective, less invasive, prosthetic delivery systems, particularly for mitral valve replacement.

For example, it may be desirable to utilize a trans-septal approach to the native mitral valve with a catheter-based delivery system. To reach the native mitral valve, the delivery catheter may be inserted through the femoral vein into the common iliac vein, through the inferior vena cava, and into the right atrium. Alternatively, the delivery catheter may be inserted into the subclavian vein, through the superior vena cava, and into the right atrium. In either approach, the septal wall between the right atrium and the left atrium is punctured with a guidewire or other puncturing device. The distal tip component of the delivery catheter is advanced through the septal perforation and into the left atrium, and placed in proximity to the annulus of the native mitral valve. Generally, the delivery catheter is manipulated such that the distal tip component of the catheter extends through the native mitral valve and into the left ventricle. The delivery catheter can then be manipulated to deploy the heart valve prosthesis, such as, for example, from a capsule or sheath of the delivery catheter. However, when deploying some types of heart valve prostheses, manipulation of the capsule to deploy the heart valve prosthesis, or portions thereof, may be difficult due to limited space within the left ventricle.

Accordingly, there is a need for catheter-based delivery systems that may be advanced to a native mitral valve via a trans-septal approach and that provide for a successful deployment of a replacement mitral valve in the limited space of the left ventricle.

BRIEF SUMMARY OF THE INVENTION

Embodiments hereof relate to a delivery system for percutaneously delivering a heart valve prosthesis to a site of a native valve. The delivery system includes a heart valve prosthesis and a delivery catheter. The heart valve prosthesis includes an anchoring member at least partially surrounding and coupled to an inner valve support. The heart valve prosthesis includes a radially collapsed configuration and a radially expanded configuration. The delivery catheter includes a delivery configuration and a release configuration. The delivery catheter includes an outer shaft, an intermediate shaft disposed through a lumen of the outer shaft, and an inner shaft disposed through a lumen of the intermediate shaft. In the delivery configuration the outer shaft retains the anchoring member of the heart valve prosthesis in a radially compressed state for delivery to a treatment site and the intermediate shaft retains at least a portion of the inner valve support of the heart valve prosthesis in a radially compressed state for delivery to a treatment site; and Embodiments hereof also relate to a delivery catheter for percutaneously delivering a heart valve prosthesis to a site of a native valve. The delivery catheter includes a handle, an outer shaft operably coupled to the handle such that the outer shaft is axially slidable relative to the handle, an intermediate shaft disposed within a lumen of the outer shaft, and an inner shaft disposed within a lumen of the intermediate shaft. The intermediate shaft is operably coupled to the handle such that the intermediate shaft is axially slidable relative to the handle. The inner shaft is coupled to the handle. The outer shaft is axially slidable relative to the intermediate shaft and the inner shaft. The intermediate shaft is axially slidable relative to the outer shaft and the inner shaft. The outer shaft and the intermediate shaft are configured in combination to retain a heart valve prosthesis in a radially compressed configuration.

Embodiments hereof further relate to a method of delivering and positioning a heart valve prosthesis at a site of a native valve. The method includes positioning a delivery catheter at a site of a native heart valve with the heart valve prosthesis in a radially compressed configuration. The heart valve prosthesis includes an outer member coupled to an inner member, and a prosthetic valve component coupled to the inner member. The delivery catheter includes an outer shaft, an intermediate shaft, and an inner shaft configured in combination to hold the heart valve prosthesis in the radially compressed configuration. The method further includes retracting the outer shaft to release the outer member of the heart valve prosthesis from the outer shaft such that the outer member radially expands. After the step of retracting the outer shaft, the intermediate shaft is retracted to release the inner member of the heart valve prosthesis from the intermediate shaft such that the inner member radially expands.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of delivery systems for delivering a heart valve prosthesis within a native mitral valve, the delivery system described herein can also be used in other valves of the body, non-limiting examples of which include delivering a heart valve prosthesis within a native tricuspid valve, a native aortic valve, a native pulmonary valve, or for delivering a heart valve prosthesis within a failed previously implanted heart valve prosthesis. Furthermore, there is no intention to be bound by any expressed or implied theory presented in the preceding technical field, background, and brief summary or the following detailed description.

Figure 1:
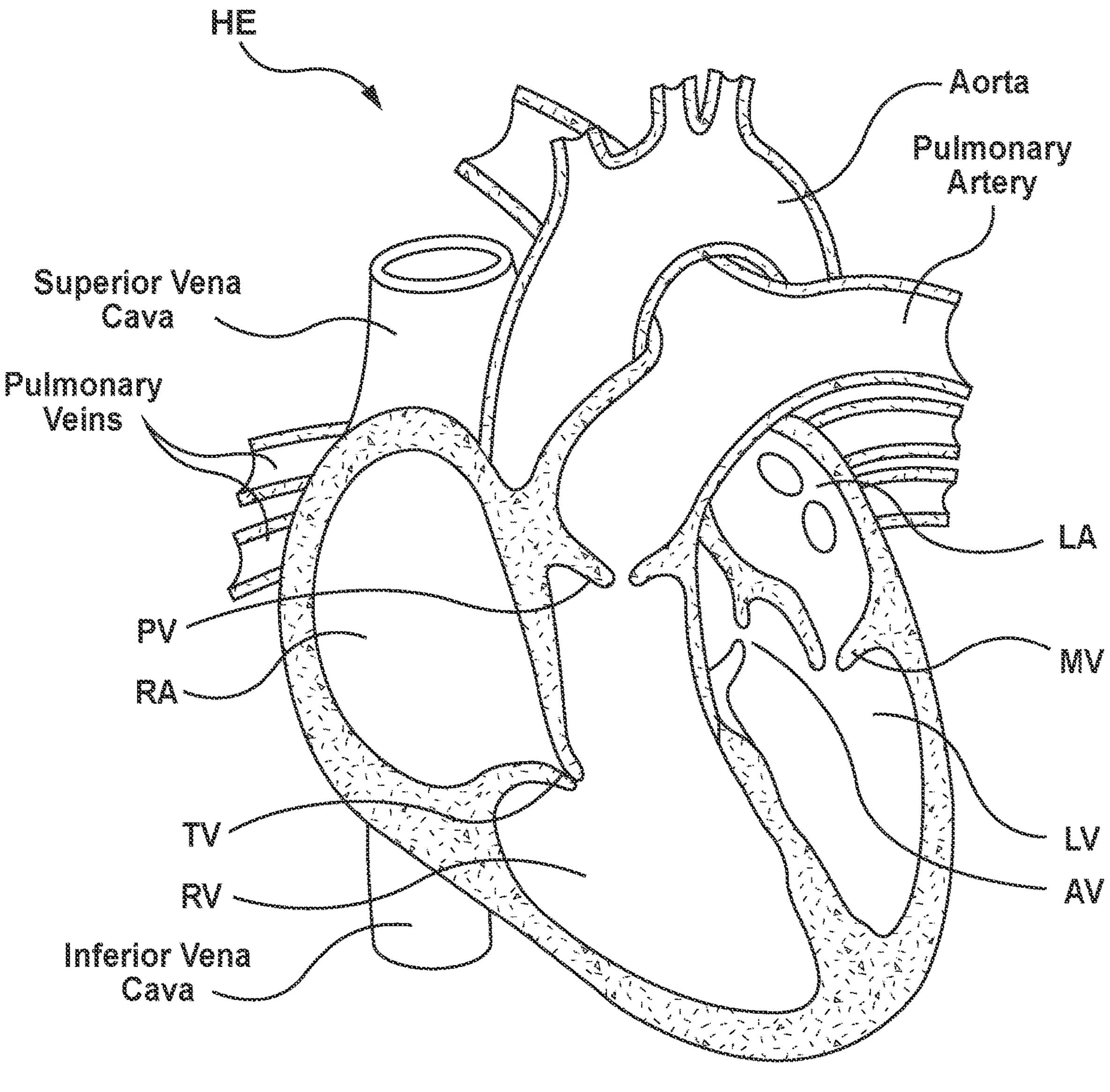
FIG. 1 depicts a schematic sectional view of a mammalian heart having native valve structures.
Figure 2B:
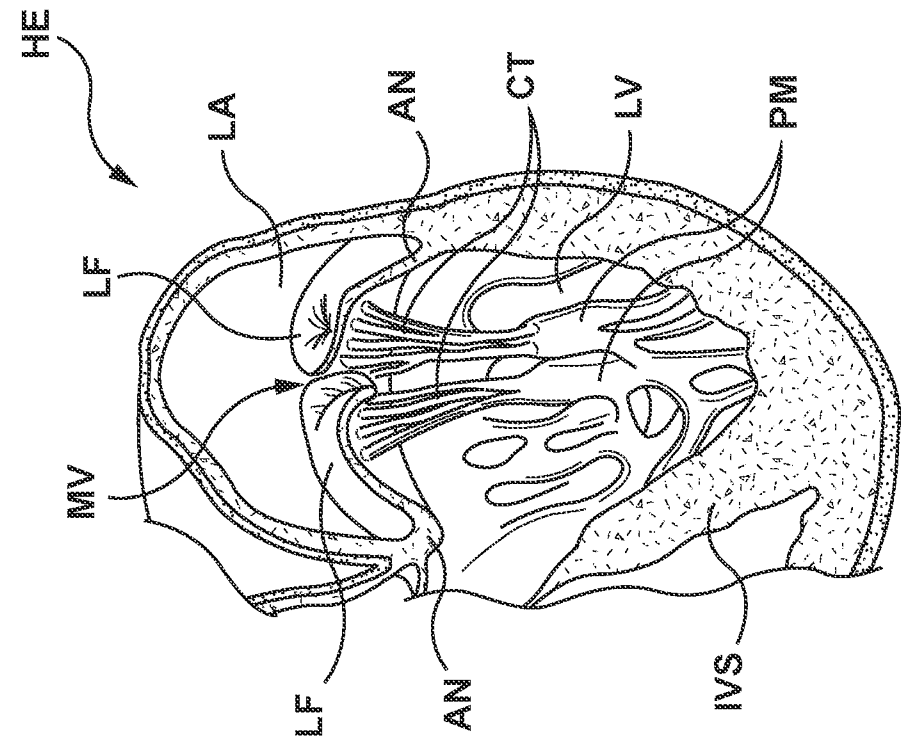
FIG. 2B depicts a schematic sectional view of the left ventricle of a heart having a prolapsed mitral valve in which the leaflets do not sufficiently co-apt and which is suitable for replacement with a heart valve prosthesis via a delivery system in accordance with embodiments hereof.
Figure 2A:
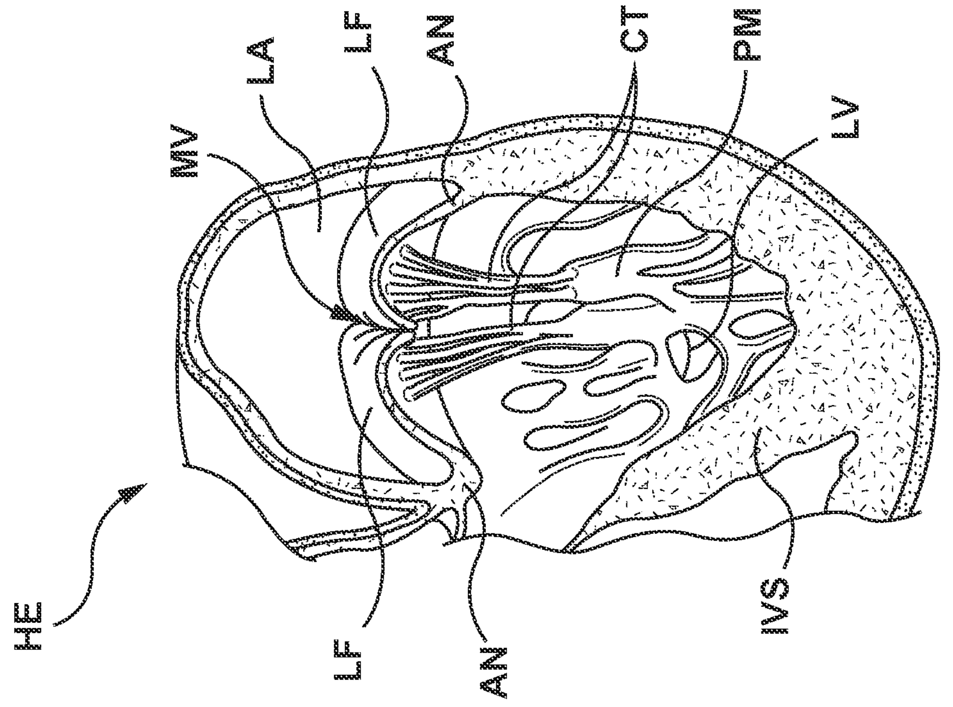
FIG. 2A depicts a schematic sectional view of a left ventricle of a mammalian heart showing anatomical structures and a native mitral valve.

FIG. 1 is a schematic sectional illustration of a mammalian heart HE that depicts the four heart chambers (right atrium RA, right ventricle RV, left atrium LA, left ventricle LV) and native valve structures (tricuspid valve TV, mitral valve MV, pulmonary valve PV, aortic valve AV). FIG. 2A is a schematic sectional illustration of a left ventricle LV of a mammalian heart HE showing anatomical structures and a native mitral valve MV. Referring to FIGS. 1 and 2A together, the heart HE includes the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, as shown in FIG. 2A, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN which is distinct from both the tissue of the leaflets LF as well as the adjoining muscular tissue of the heart wall. In general, the connective tissue at the annulus AN is more fibrous, tougher and stronger than leaflet tissue. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart HE having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Figure 3A:
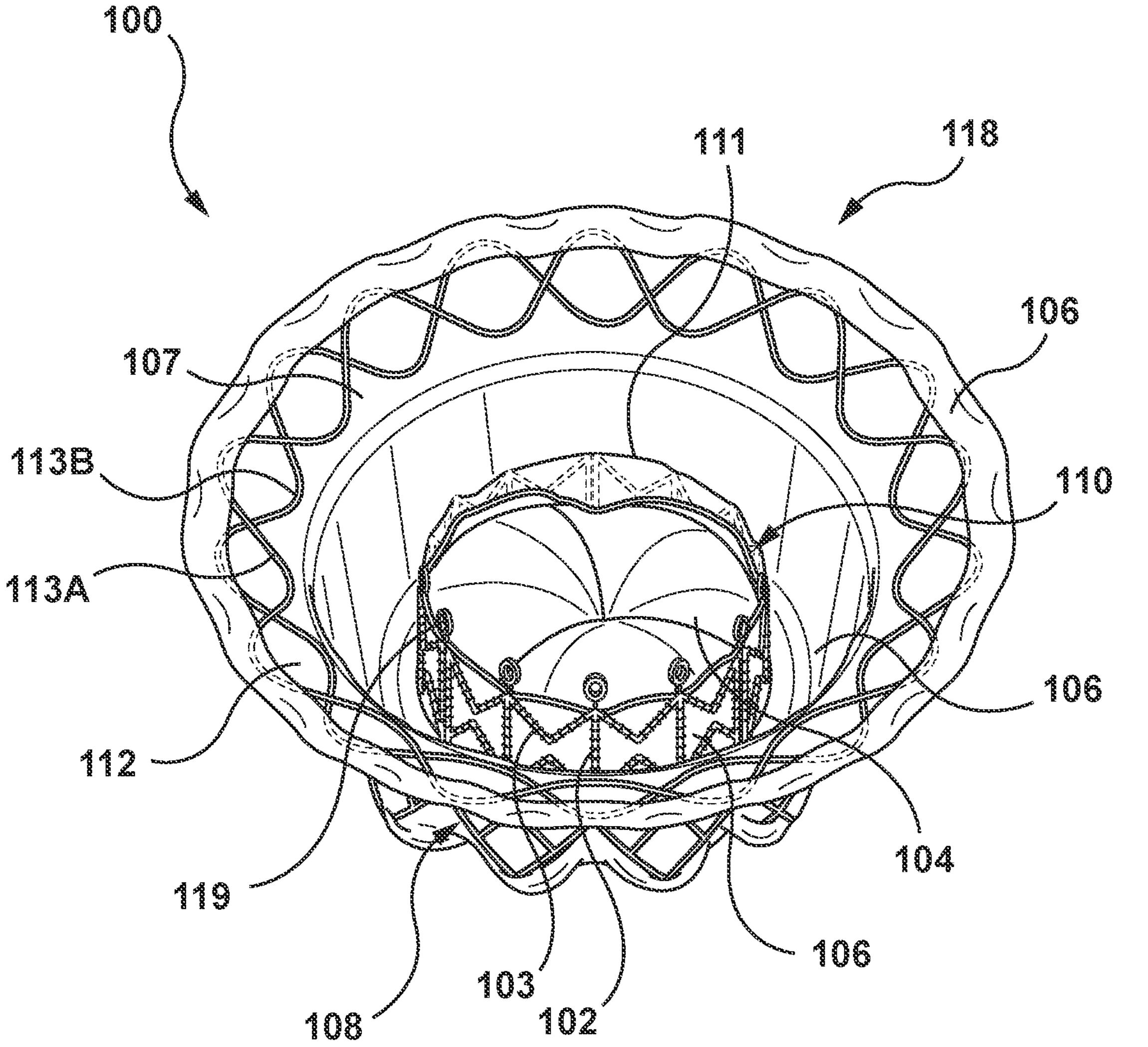
FIG. 3A depicts a perspective view of a heart valve prosthesis in a radially expanded configuration.
Figure 3C:
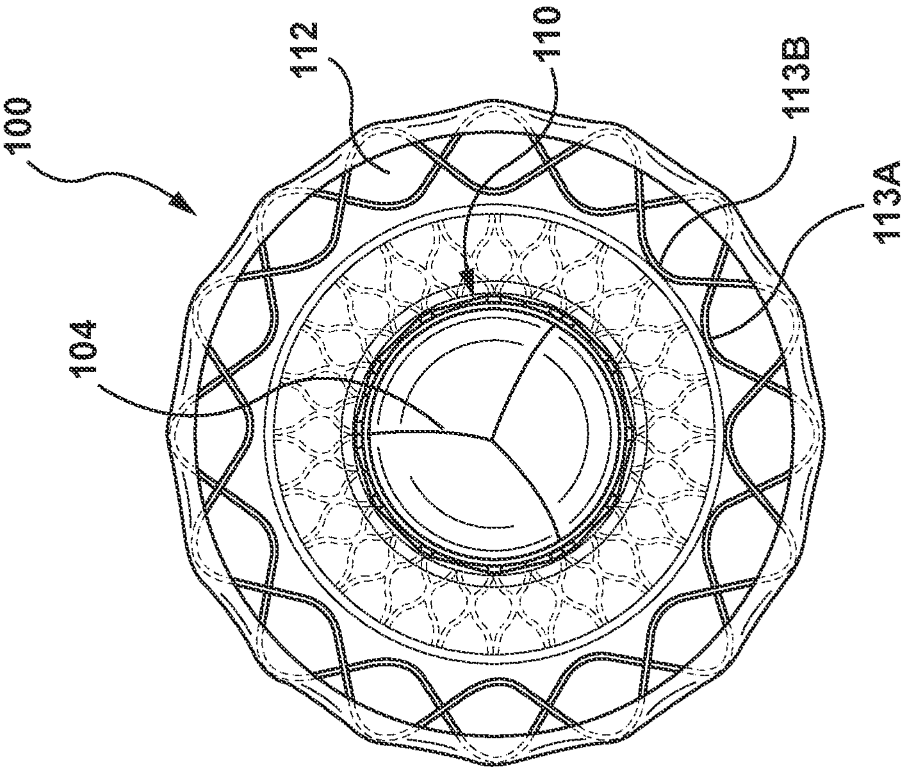
FIG. 3C depicts a top view of the heart valve prosthesis of FIG. 3A in the radially expanded configuration.
Figure 3B:
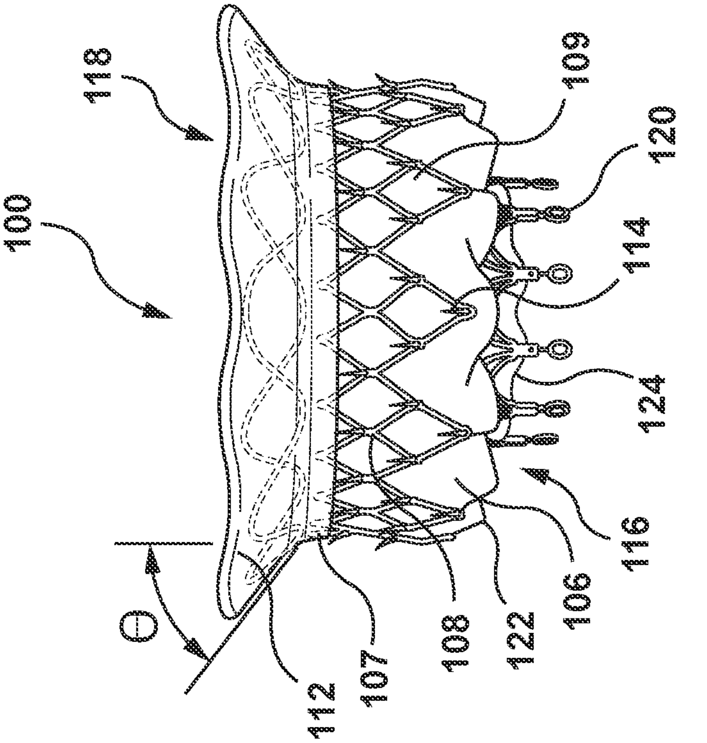
FIG. 3B depicts a side view of the heart valve prosthesis of FIG. 3A in the radially expanded configuration.

FIGS. 3A, 3B, 3C are perspective, side, and top views, respectively, of an exemplary heart valve prosthesis 100 for use in embodiments hereof, wherein the heart valve prosthesis 100 is in an expanded or deployed configuration. The heart valve prosthesis 100 is illustrated herein in order to facilitate description of delivery catheters and systems to be utilized in conjunction therewith according to embodiments hereof. It is understood that any number of alternate heart valve prostheses can be used with the methods and devices described herein. The heart valve prosthesis 100 is merely exemplary and is similar to heart valve prostheses described in more detail in U.S. Pat. No. 9,034,032 to McLean et al., and WIPO Publication No. WO 2014/144937 to Morriss et al., each of which is incorporated by reference herein in its entirety. However, this is not meant to be limiting, and the delivery systems, catheter, and methods described herein may be used with other heart valve prostheses. The systems and methods described herein are particularly useful for heart valve prostheses with inner and outer components.

Figure 4:
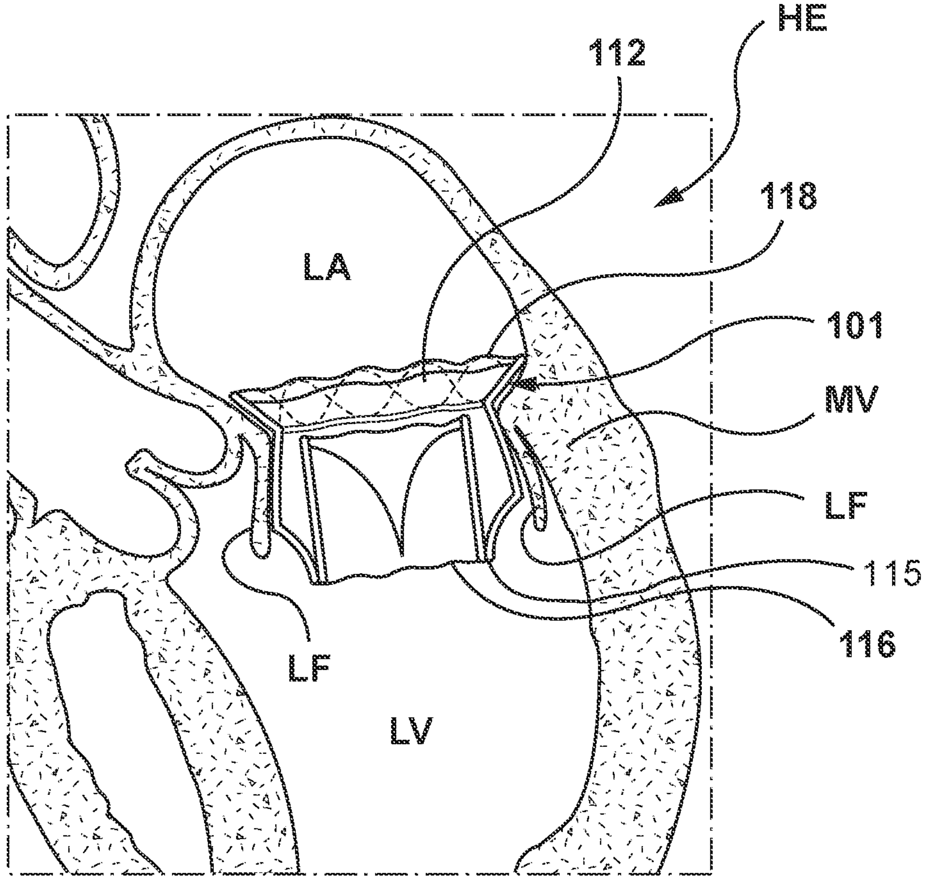
FIG. 4 depicts a sectional view of the heart valve prosthesis of FIG. 3A implanted within an annulus of a native mitral valve.
Figure 8:
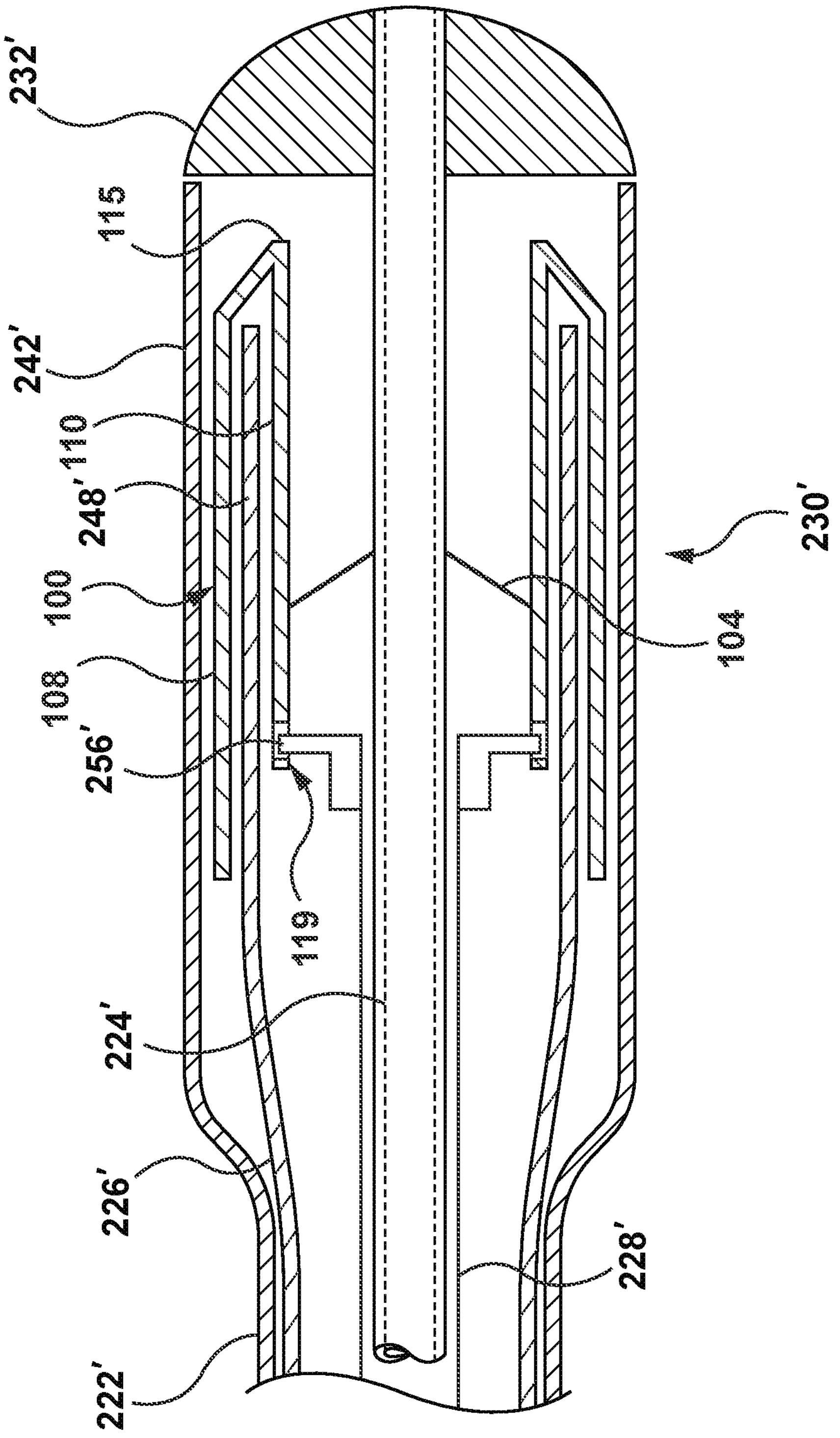
FIG. 8 depicts a sectional view of a distal portion of the delivery system of FIG. 7, wherein the heart valve prosthesis is shown in a radially compressed configuration

As shown in FIGS. 3A-3C, the heart valve prosthesis 100 includes a flexible outer or anchoring member 108 at least partially surrounding and coupled to an inner member or inner valve support 110 at a joint 115 (see FIG. 4). The heart valve prosthesis 100 further includes a prosthetic valve component 104 coupled to, mounted within, or otherwise carried by the inner valve support 110. The heart valve prosthesis 100 is configured for placement within a native mitral valve and includes a downstream end or outflow portion 116 and an upstream end or inflow portion 118. The heart valve prosthesis 100 also includes one or more sealing members 106 and tissue engaging elements 114. For example, the tissue engaging elements 114 may be spikes or barbs disposed on an outer wall or surface of the anchoring member 108 that extend in an upward and/or radially outward direction to engage, and in some embodiments, penetrate the native tissue to facilitate retention or to maintain position of the device in a desired implanted location. In another specific embodiment, the sealing members 106 may extend around an inner wall or surface of the anchoring member 108 and/or around an inner wall or surface of the inner valve support 110 to prevent paravalvular leaks between the heart valve prosthesis 100 and the native tissue and/or between the anchoring member 108 and the inner valve support 110. Additionally, the heart valve prosthesis may have coupling features, such as a plurality of eyelets 119 at an inflow end of the inner valve support 110 and/or a plurality of eyelets 120 at an outflow end of the heart valve prosthesis 100. In some embodiments (not shown), the coupling features may comprise one or more coupling posts or members, defined, for example, by the inner valve support. The coupling features may be used to facilitate loading, retention and deployment of the heart valve prosthesis 100 within and from a delivery catheter, as further described herein. In some embodiments, the eyelets 119 and/or 120 may not be utilized. For example, as shown in FIG. 8, described below, the plurality of eyelets 120 are not utilized.

The anchoring member 108 is a generally tubular stent, frame, or scaffold. In the embodiment shown in FIGS. 3A-3C, the anchoring member 108 has a funnel-like or hyperboloid shape or profile including an inflow portion 107 and an outflow portion 122. Further, in the embodiment shown in FIGS. 3A-3C, the anchoring member 108 is a generally tubular stent, frame, or scaffold with diamond-shaped openings 109 that may be formed by a laser-cut manufacturing method and/or another conventional stent/scaffold forming method as would be understood by one of ordinary skill in the art. For example, the anchoring member 108 may be laser cut from a single metal tube into the desired geometry, creating a tubular scaffold of interconnected struts that form the diamond-shaped openings 109. The anchoring member 108 may then be shaped into a desired configuration, e.g. funnel-like or hyperboloid shape, using known shape-setting techniques for such materials. The stent, frame, or scaffold of the heart valve prosthesis 100 may have other configurations such as a metallic, polymeric, or fabric mesh or a woven construction. In another embodiment, the anchoring member 108 may include a plurality of posts connected circumferentially by a plurality of struts as described herein with respect to the inner valve support 110.

The heart valve prosthesis 100 further includes a brim 112. The brim 112 is disposed at the inflow portion 118 of the heart valve prosthesis 100 and is attached to and extends from the inflow portion 107 of the anchoring member 108. The brim 112 is a flared lip or ridge of the anchoring member 108 that extends at least partially radially outward relative to the anchoring member 108. As formed and as best shown in the side view of FIG. 3B, the brim 112 may be disposed at an angle Θ relative to the outer wall or surface of the anchoring member 108, with the angle Θ ranging between 30 degrees and 90 degrees. In an embodiment hereof, the angle Θ is approximately 45 degrees, wherein "approximately" as used herein includes a tolerance of 5 degrees. In the embodiment shown in FIGS. 3A-3C, the brim 112 includes two sinusoidal rings 113A, 113B and the sealing member 106 disposed over or covering at least a downstream surface of the sinusoidal rings 113A, 113B. The sinusoidal rings 113A, 113B are disposed out of phase relative to each other, and may be woven together or may be disposed in an overlapping manner and coupled together.

The inner valve support 110 is also a generally tubular stent, frame, or scaffold that supports the prosthetic valve component 104 within the interior thereof. The inner valve support 110 includes an inflow portion 111 and an outflow portion 124. In some embodiments, the inner valve support 110 includes a plurality of posts 102 connected circumferentially by a plurality of struts 103. The posts 102 and the struts 103 may be arranged in a variety of geometrical patterns that may expand and provide sufficient resilience and column strength for maintaining the integrity of the prosthetic valve component 104. For example, the posts 102 may extend longitudinally across multiple rows of the struts 103 to provide column strength to the inner valve support 110. Generally, the plurality of posts 102 may extend along an axial direction generally parallel to a longitudinal axis LA and the plurality of struts 103 may extend circumferentially around and transverse to the longitudinal axis LA. As will be understood by persons skilled in the pertinent art, the stent, frame, or scaffold of the inner valve support 110 may have other configurations such as a metallic, polymeric, or fabric mesh or a woven construction. In another embodiment hereof, the inner valve support 110 may be laser cut from a single metal tube into the desired geometry, creating a tubular scaffold of interconnected struts.

In embodiments hereof, both the anchoring member 108 and the inner valve support 110 are self-expanding to return to a radially expanded or deployed state from a radially compressed or constricted state and may be made from stainless steel, a pseudo-elastic metal such as a nickel-titanium alloy (e.g. NITINOL), or a so-called super alloy, which may have a base metal of nickel, cobalt, chromium, or other metal. "Self-expanding" as used herein means that a structure/component has a mechanical memory to return to the expanded or deployed configuration as described herein. Alternatively, one or more portions of the heart valve prosthesis 100 may be self-expanding, balloon-expandable and/or mechanically expandable as would be understood by persons skilled in the pertinent art. Whether the heart valve prosthesis 100 is self-expanding, mechanically expandable, and/or balloon-expandable, the heart valve prosthesis 100 has a radially compressed configuration for delivery within a delivery catheter and a radially expanded configuration for deployment within an annulus of a native heart valve.

As previously mentioned, the heart valve prosthesis 100 includes the prosthetic valve component 104 within the interior of the inner valve support 110. In an embodiment, the prosthetic valve component 104 may be positioned adjacent to the inflow portion 111 of the inner valve support 110. The prosthetic valve component 104 is configured as a one-way valve to allow blood flow in one direction and thereby regulate blood flow through the prosthetic valve component 104. Thus, the prosthetic valve component 104 is capable of blocking flow in one direction via valve leaflets that may form, for example, a bicuspid or tricuspid replacement valve. More particularly, if the heart valve prosthesis 100 is configured for placement within a native valve having two leaflets, such as the mitral valve, the prosthetic valve component 104 may include two valve leaflets to form a bicuspid replacement valve that closes with pressure on the outflow and opens with pressure on the inflow. In other embodiments, the prosthetic valve component 104 may be a tricuspid replacement valve or may be a single leaflet replacement valve. However, the number of leaflets of the valve component 104 of the heath valve prosthesis 100 need not match the number of native leaflets of the native valve in which the heart valve prosthesis 100 is to be deployed. The valve leaflets are sutured or otherwise securely and sealingly attached to an inner circumference of the inner valve support 110 and/or the sealing member 106 which encloses or lines the inner valve support 110, as will be understood by persons skilled in the pertinent art.

The valve leaflets may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

The sealing members 106 may be formed from a suitable graft material such as a natural or biological material such as pericardium or another membranous tissue such as intestinal submucosa. Alternatively, the sealing members 106 may be a low-porosity woven fabric, such as polyester, DACRON® polyester fabric, or polytetrafluoroethylene (PTFE), which creates a one-way fluid passage when attached to the stent. In one embodiment, the sealing members 106 may be a knit or woven polyester, such as a polyester or polytetrafluoroethylene (PTFE) knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side.

FIG. 4 is an illustration of the heart valve prosthesis 100 implanted within a native mitral valve MV of a heart HE, which is shown in section. The heart valve prosthesis 100 is shown deployed within the native mitral valve MV, with the downstream end or outflow portion 116 thereof extending into the left ventricle LV and the upstream end or inflow portion 118 including at least the brim 112 thereof extending into the left atrium LA. When the heart valve prosthesis 100 is deployed within the valve annulus of a native heart valve, in this example the native mitral valve MV, the inner valve support 110 and the anchoring member 108 expand within the native valve leaflets LF of the patient's defective valve, retaining the native valve leaflets LF in a permanently open state.

A delivery system in accordance with the embodiments hereof includes a delivery catheter or device and a heart valve prosthesis (e.g., heart valve prosthesis 100 described above) mounted at a distal portion of the delivery catheter. The delivery catheter generally includes multiple shafts to sequentially deploy different corresponding portions of a heart valve prosthesis.

Figure 5:
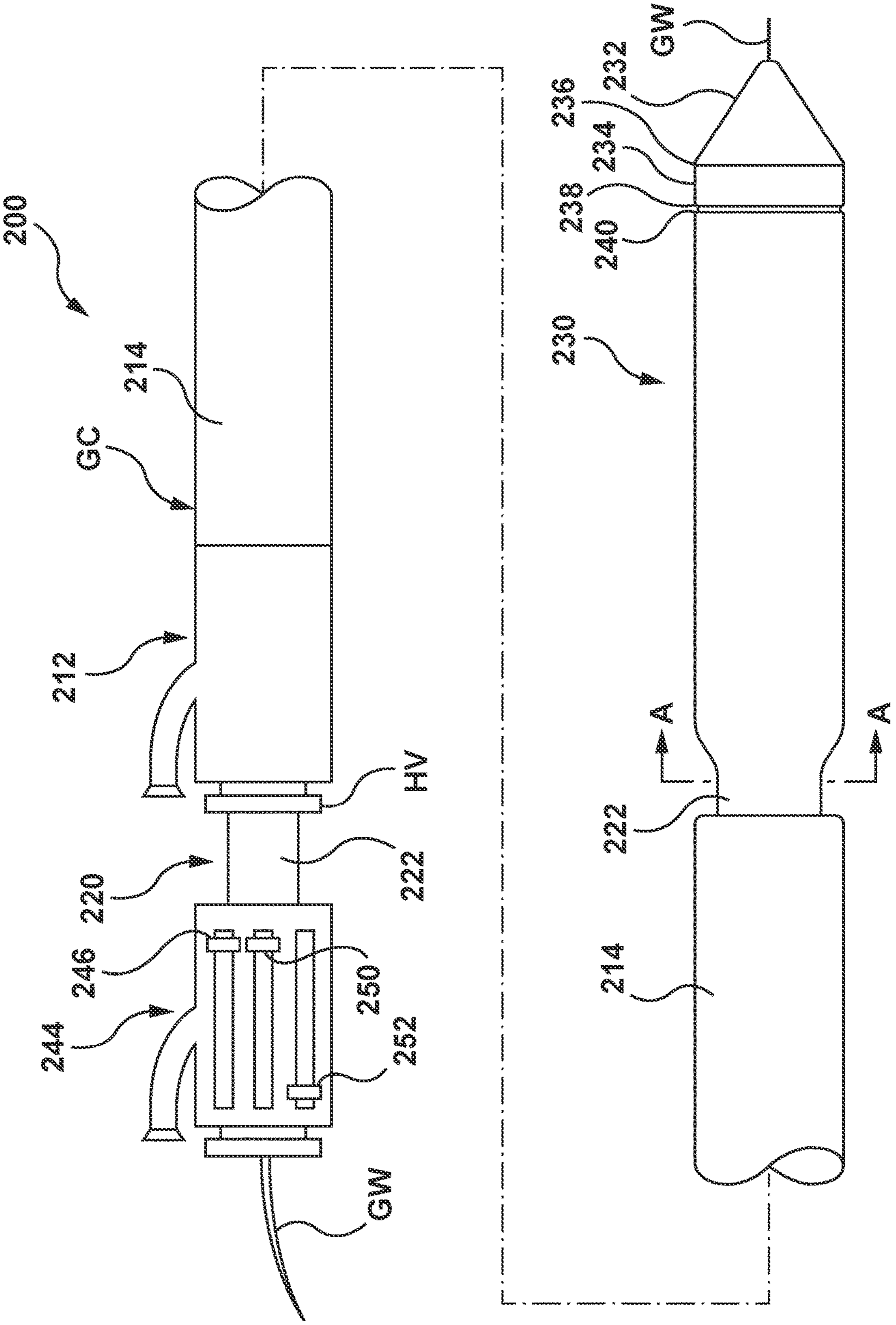
FIG. 5 depicts a side view of a delivery system configured to deliver a heart valve prosthesis in accordance with an embodiment hereof.
Figure 6:
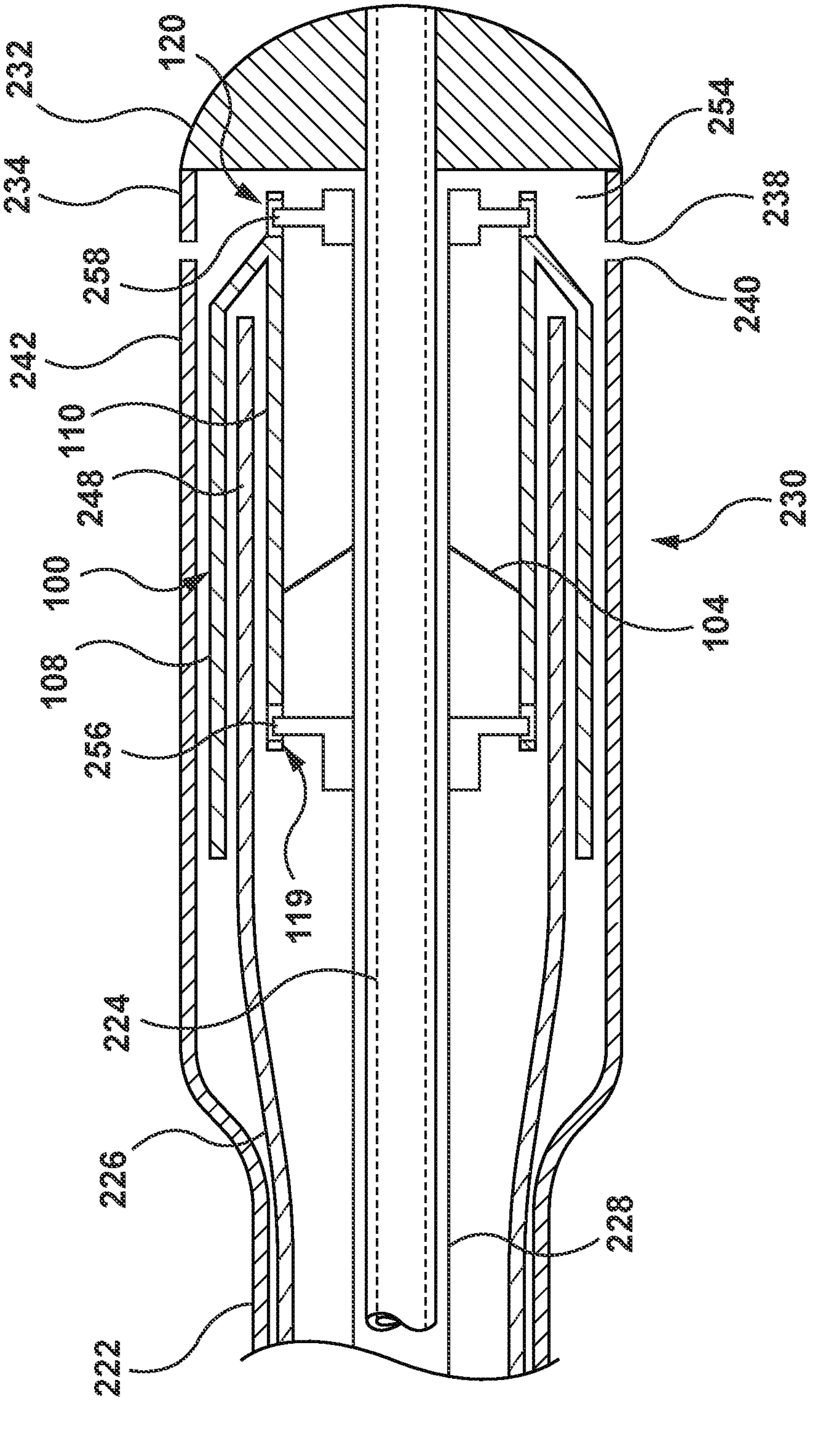
FIG. 6 depicts a sectional view of a distal portion of the delivery system of FIG. 5, wherein the heart valve prosthesis is shown in a radially compressed configuration.

In an embodiment shown in FIG. 5, a delivery system 200 includes an introducer sheath or guiding catheter GC and a delivery catheter 220 and a heart valve prosthesis such as the heart valve prosthesis 100 described previously (not visible in FIG. 5 but visible in FIG. 6). The introducer sheath or guiding catheter GC may include a handle 212 coupled to a delivery shaft 214, which in one embodiment is 34 French or less, and in another embodiment, 28 French or less in diameter. The introducer sheath or guiding catheter GC may be steerable or pre-shaped in a configuration suitable for the particular approach to the target valve. The introducer sheath or guiding catheter GC may be expandable. The delivery catheter 220 is placed through a hemostasis valve HV on a proximal end of the introducer sheath or guiding catheter GC. Alternatively, the introducer sheath or guiding catheter GC may be configured as an in-line introducer sheath or guiding catheter GC such that delivery catheter 220 is not removable from the introducer sheath or guiding catheter GC.

Figure 5A:
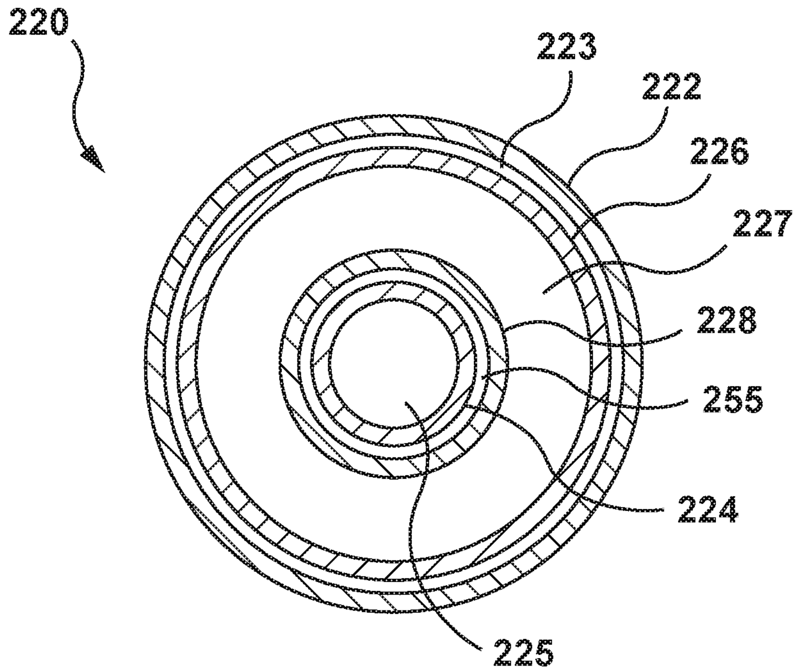
FIG. 5A depicts a cross-sectional view of the delivery system taken along line A-A of FIG. 5.

The delivery catheter 220 is depicted in a delivery configuration in FIG. 5 with the heart valve prosthesis 100 (not visible in FIG. 5 but visible in FIG. 6) loaded within a capsule portion 230. The delivery catheter 220, as shown in FIG. 5A, includes a first or outer shaft 222 including a lumen 223 therethrough, a second or inner shaft 224 including a guidewire lumen 225 therethrough, and a third or intermediate shaft 226 disposed between the inner shaft 224 and the outer shaft 222 and including a lumen 227 therethrough. The guidewire lumen 225 may be sized to slidingly receive a guidewire GW such that the delivery catheter 220 may be tracked over the guidewire GW during delivery of the heart valve prosthesis 100. The outer shaft 222, the inner shaft 224, and the intermediate shaft 226 are configured to slide relative to each other. As shown in FIG. 5A, and explained in more detail below, the delivery catheter 220 may also include a spindle shaft 228 disposed between the inner shaft 224 and the intermediate shaft 226. The spindle shaft 228 includes a plurality of coupling features, for example, spindle pins 256 (not visible in FIG. 5A but visible in FIG. 6) configured to couple with eyelets 119 to maintain the longitudinal or axial position of the heart valve prosthesis 100 when the heart valve prosthesis 100 is in the radially compressed configuration within the capsule portion 230, as explained in more detail below. Referring back to FIG. 5, the delivery catheter 220 may also include a nosecone or distal tip component 232 attached to a distal end of the inner shaft 224. A distal shaft component 234 may be included that extends proximally from the distal tip component 232. The distal shaft component 234 includes a distal end 236 coupled to the distal tip component 232 and a proximal open end 238 that faces a distal open end 240 of the outer shaft 222. Although a small gap is shown in FIGS. 5 and 6 between the distal open end 240 of the outer shaft 222 and the proximal open end 238 of the distal shaft component 234, this is for illustration purposes and the ends 238, 240 may abut against each other in the delivery configuration.

With reference to FIG. 5A, the lumen 223 of the outer shaft 222 is sized to slidably receive the intermediate shaft 226. The outer shaft 222 further includes a capsule segment 242 which forms a distalmost portion or segment of the outer shaft 222, as shown in FIG. 6. The capsule segment 242 functions to protect, secure, and compressively retain the anchoring member 108 of the heart valve prosthesis 100 for delivery. More particularly, the capsule segment 242 is configured to encircle the anchoring member 108 and to thereby hold or compressively retain the anchoring member 108 in a radially compressed state for delivery to a treatment site. The outer shaft 222 is axially slidable relative to the intermediate shaft 226, the spindle shaft 228, and the inner shaft 224. Thus, to release and deploy the anchoring member 108 from the capsule segment 242, the outer shaft 222 is proximally retracted such that the capsule segment 242 does not encircle the anchoring member 108. In order to axially slide the outer shaft 222 relative to the intermediate shaft 226, the spindle shaft 228, and the inner shaft 224, the outer shaft 222 is coupled to a first actuator 246 on a handle 244 of the delivery catheter 220, as shown in FIG. 5. Various first actuators 246 may be used, such as an axially-slidable lever, a rotatable rack and pinion gear, or other known mechanisms. The heart valve prosthesis 100 is oriented in the delivery catheter such that the brim 112 faces proximally within the delivery catheter 220.

While the capsule segment 242 is described herein as an integral or continuous distalmost portion or segment of the outer shaft 222, this is not meant to be limiting. In another embodiment hereof (not shown), the capsule segment 242 may be formed as a separate component from the outer shaft 222 coupled to the outer shaft 222. In another embodiment hereof (not shown), capsule segment 242 may be an integral or continuous distalmost portion or segment of the outer shaft 222 in that capsule segment 242 has the same continuous cross-sectional diameter as the outer shaft 222.

As also shown in FIG. 5A, the lumen 227 of the intermediate shaft 226 is sized to receive the spindle shaft 228. The intermediate shaft 226 further includes a capsule segment 248 which forms a distalmost portion or segment of the intermediate shaft 226, as best shown in FIG. 6. The capsule segment 248 functions to protect, secure, and compressively retain the inner valve support 110 of the heart valve prosthesis 100 for delivery. Specifically, the capsule segment 248 is configured to encircle the inner valve support 110 proximal of the joint 115 and to thereby hold or compressively retain the inner valve support 110 in a radially compressed state for delivery to a treatment site. Thus, as can be seen in FIG. 6, the capsule segment 248 of the intermediate shaft is disposed between the anchoring member 108 and the inner valve support 110 when the heart valve prosthesis 100 is in the radially compressed configuration within the capsule 230 of the delivery catheter 220. The intermediate shaft 226 is axially slidable relative to the outer shaft 222, the spindle shaft 228, and the inner shaft 224. To release and deploy the inner valve support 110, the intermediate shaft 226 is proximally retracted such that the capsule segment 248 does not encircle the inner valve support 110. In order to axially slide the intermediate shaft 226 relative to the outer shaft 222, the spindle shaft 228, and the inner shaft 224, the intermediate shaft 226 is coupled to a second actuator 250 on the handle 244 of the delivery catheter 220, as shown in FIG. 5. Various second actuators 250 may be used, such as an axially-slidable lever, a rotatable rack and pinion gear, or other known mechanisms.

The capsule segment 248 is described herein as an integral or continuous distalmost portion or segment of the intermediate shaft 226. However, this is not meant to be limiting, and in another embodiment hereof (not shown), the capsule segment 248 is formed as a separate component from the intermediate shaft 226 and coupled thereto. In another embodiment hereof (not shown), capsule segment 248 may be an integral or continuous distalmost portion or segment of the intermediate shaft 226 in that capsule segment 248 has the same continuous cross-sectional diameter as the intermediate shaft 226. Further, in embodiments wherein the delivery catheter 220 does not include a spindle shaft 228, the lumen 227 of the intermediate shaft 226 is sized to slidably receive the inner shaft 224.

In the embodiment of FIGS. 5-6, the delivery catheter 220 further includes the spindle shaft 228. The spindle shaft 228 includes a lumen 255 sized to slidably receive the inner shaft 224, as shown in FIG. 5A. A proximal portion of the spindle shaft 228 is rigidly coupled to the handle 244 such that movement of the handle 244 correspondingly moves the spindle shaft 228. The spindle shaft 228 further includes a plurality of coupling features such as, for example, a plurality of proximal spindle pins 256 and/or a plurality of distal spindle pins 258 on a distal portion thereof extending radially outward from an outer surface of the spindle shaft 228, as shown in FIG. 6. The spindle shaft 228, and more precisely the plurality of proximal spindle pins 256 and/or the plurality of distal spindle pins 258 of the spindle shaft 228, is configured to couple with the coupling features of the heart valve prosthesis 100, for example, the plurality of eyelets 119 and/or 120, to maintain the longitudinal position of the heart valve prosthesis 100 in relation to the spindle shaft 228, and indirectly to the handle 244 of the delivery catheter 220 as the delivery catheter 220 transitions from the delivery configuration to the release configuration. More precisely, when the heart valve prosthesis 100 is disposed in the radially compressed configuration within the capsule portion 230 of the delivery catheter 200, the plurality of proximal spindle pins 256 extend through a corresponding plurality of eyelets 119 of the heart valve prosthesis 100 and/or the plurality of distal spindle pins 258 extend through a corresponding plurality of eyelets 120 of the heart valve prosthesis 100. With the plurality of proximal and/or distal spindle pins 256, 258 disposed though the corresponding plurality of eyelets 119, 120, respectively, the heart valve prosthesis 100 resists longitudinal movement with respect to the spindle shaft 228. Thus, the plurality of proximal and/or distal spindle pins 256, 258 hold the heart valve prosthesis 100 in position longitudinally even as frictional forces attempt to longitudinally translate the heart valve prosthesis 100 as the outer shaft 222 and/or the intermediate shaft 226 are translated proximally and/or distally.

Each proximal and distal spindle pin 256, 258 includes a smooth outer surface that enables unencumbered expansion of the heart valve prosthesis 100 from the radially compressed configuration to the radially expanded configuration. While illustrated herein with a specific number of proximal and distal spindle pins 256, 258, this is not meant to be limiting, and more or fewer proximal and/or distal spindle pins 256, 258 may be utilized in any combination.

The coupling features of the spindle shaft 228 are described herein, for example, as a plurality of proximal and/or distal spindle pins 256, 258. However, this is not meant to be limiting, and in another embodiment hereof (not shown), the spindle shaft 228 may include coupling features such as, for example, recesses, grooves, or cut-outs that correspond to the coupling features of the heart valve prosthesis 100, such as, for example, coupling posts or members.

The inner shaft 224 may include the guidewire lumen 225, as best shown in FIG. 5A. A distal portion of the inner shaft 224 is coupled to the distal tip component 232, as shown in FIG. 6. The inner shaft 224 is configured to transmit movement from the inner shaft 224 to the distal tip component 232. The inner shaft 224 is axially slidable relative to the outer shaft 222, the intermediate shaft 226, and the spindle shaft 228. More specifically, and as shown in FIG. 5, the inner shaft 224 is coupled to a third actuator 252 on the handle 244 of the delivery catheter 220. Actuation of the third actuator 252 axially slides the inner shaft 224 relative to the outer shaft 222, the intermediate shaft 226, and the spindle shaft 228. Various third actuators 252 may be used, such as an axially-slidable lever, a rotatable rack and pinion gear, or other known mechanisms.

In the embodiment of FIG. 6, the distal tip component 232 includes the distal shaft component 234, as described previously. The distal shaft component 234 forms a proximal portion of the distal tip component 232 and defines a recess 254 between the distal end 236 and the proximal end 234 that proximally faces the distal open end 240 of the outer shaft 222. The recess 254 of the distal tip component 232 is configured to encircle and retain the outflow portion 118 of the heart valve prosthesis 100 to thereby hold or compressively retain the outflow portion 118 in a radially compressed state for delivery to a treatment site. In particular, in the embodiment of FIG. 6, the distal shaft component encircles the eyelets 120 of the heart valve prosthesis 100.

Figure 7:
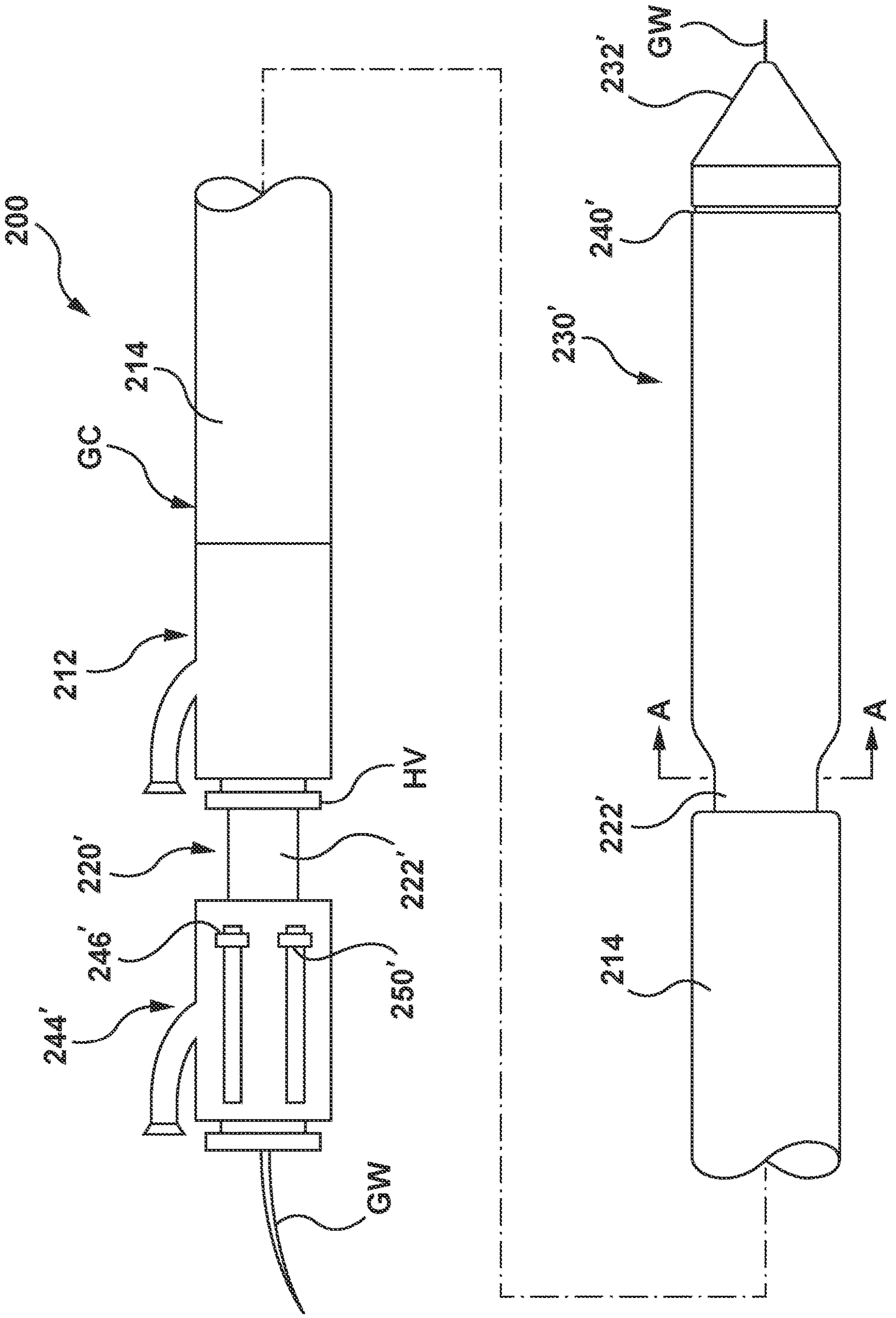
FIG. 7 depicts a side view of a delivery system configured to deliver a heart valve prosthesis in accordance with another embodiment hereof.
Figure 7A:
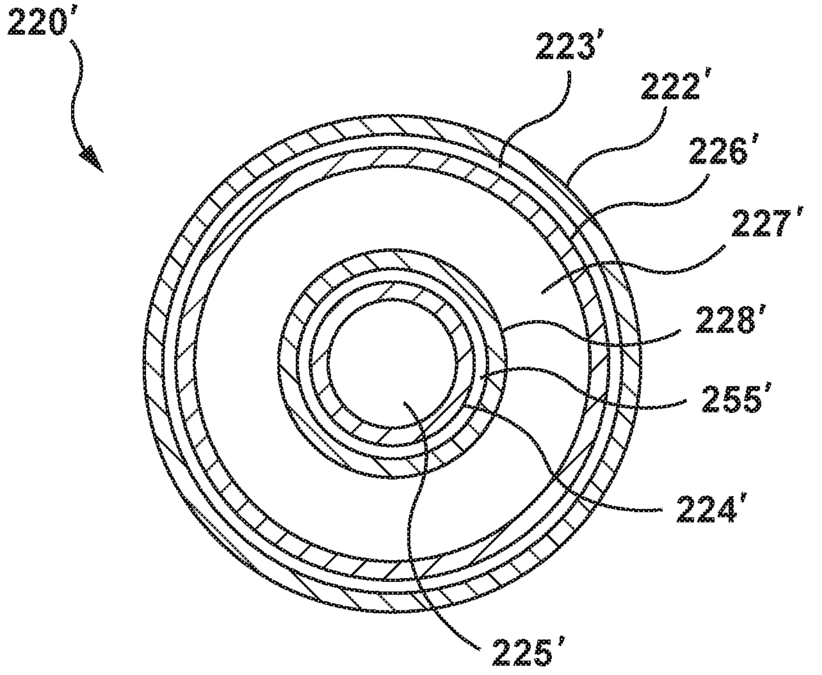
FIG. 7A depicts a cross-sectional view of the delivery system taken along line A-A of FIG. 7.

FIGS. 7-8 depict a delivery catheter 220' according to another embodiment hereof. The delivery catheter 220', as shown in FIGS. 7 and 7A, includes a first or outer shaft 222', a second or inner shaft 224', a third or intermediate shaft 226', a spindle shaft 228', a handle 244', and a distal tip component 232'. The delivery catheter 220', the outer shaft 222', the inner shaft 224', the intermediate shaft 226', the spindle shaft 228' and the handle 244' are similar to the delivery catheter 220, the outer shaft 222, the third or intermediate shaft 226, the spindle shaft 228 and the handle 244, and therefore details and alternatives of similar components will not be repeated here. However, the distal tip component 232' of the delivery catheter 220' does not include a distal shaft component extending proximally from the distal tip component 232'. Further, in the embodiment shown, the spindle shaft 228' does not include distal spindle pins 258. Moreover, the inner shaft 224' may be rigidly coupled to the handle 244'. In an alternative embodiment (not shown), inner shaft 224' is omitted and the spindle shaft 228 extends distally to and is coupled to the distal tip component 232'

In the embodiment of FIG. 8, the intermediate shaft 226', and more specifically a capsule segment 248' of the intermediate shaft 226', functions to protect, secure, and compressively retain the inner valve support 110 of the heart valve prosthesis 100 proximal of the joint 115. In the embodiment shown in FIG. 8, the eyelets 120 are not included as part of the heart valve prosthesis 100 and thus the delivery catheter 220' does not include the distal coupling features, e.g. the spindle pins 258. However, in another embodiment, the heart valve prosthesis may include the eyelets 120 at the outflow portion 118 of the heart valve prosthesis 100. In such an embodiment, the capsule segment 248' would maintain the inner valve support 110 and the eyelets 120 in the radially compressed configuration even with the eyelets 120 distal of the distal end of capsule segment 248', due to the capsule segment 248' maintaining the inner valve support 110 in the radially compressed configuration. Further, the capsule segment 248' retains a portion of the anchoring member 108 in a radially compressed state for delivery to the treatment site due to the anchoring member's connection to the inner valve support 110 at joint 115. The intermediate shaft 226' is proximally retractable relative to the outer shaft 222, the spindle shaft 228 and the inner shaft 224' to release and deploy the inner valve support 110 from capsule segment 242' and enable the anchoring member 108 to fully expand following the proximal retraction of outer shaft 222.

In an embodiment, the inner shaft 224' is rigidly coupled to the handle 244' of the delivery catheter 220 such that movement of the handle 244' correspondingly moves the inner shaft 224'. Thus, the inner shaft 224' and the distal tip component 232' are not slidable/translatable relative to the handle 244'.

The distal tip component 232' is similar to the distal tip component 232 described previously, with the exception that the distal tip component 232' of the delivery catheter 220' does not include a distal shaft segment or a defined recess facing proximally. Thus, a proximal end of the distal tip component 232' abuts the open distal end 240' of the outer shaft 222' when in the delivery configuration.

Figure 9:
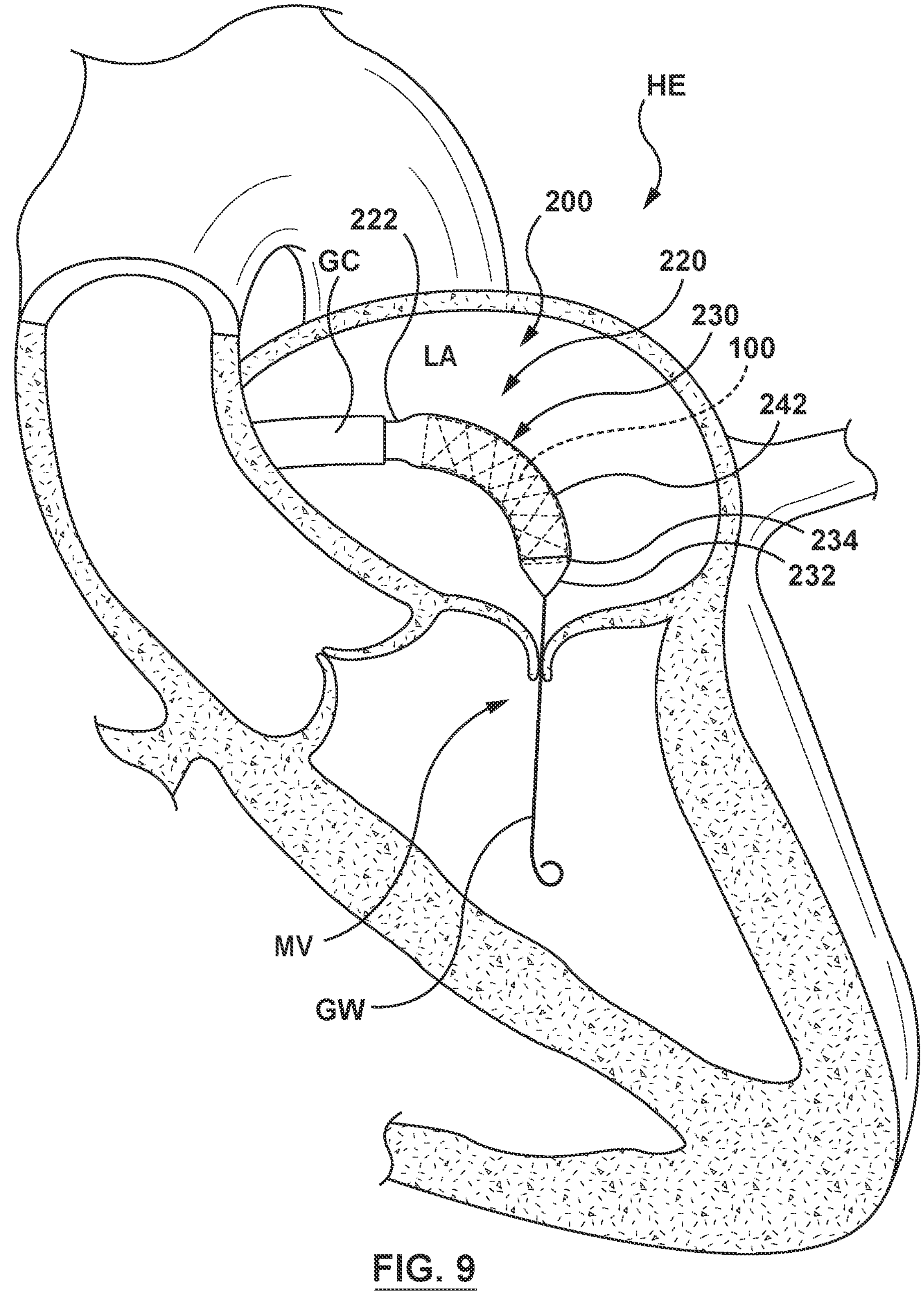
FIG. 9 is an illustration of the delivery system of FIG. 5 in situ, the delivery system being positioned into the left atrium via a trans-septal approach, wherein the heart valve prosthesis is shown in a radially compressed configuration.

FIGS. 9, 10, 11, 12, and 13 are sectional cut-away views of a heart HE illustrating a trans-septal method approach for delivering and positioning the heart valve prosthesis 100 using the delivery system 200 of FIG. 5 in accordance with an embodiment hereof. FIGS. 11A, 12A, and 13A are corresponding close-up illustrations of a distal portion of the delivery catheter 220 during the corresponding method steps of FIGS. 11, 12, and 13, respectively. With reference to FIG. 9, the delivery system 200 is shown after having been introduced into the vasculature via a percutaneous entry point technique, such as the Seldinger technique, and having been tracked through the vasculature and into the left atrium LA so that the distal tip component 232 is positioned proximate the native mitral valve MV. Intravascular access to the right atrium may be achieved via a percutaneous access site to femoral vein, into the common iliac vein, through the inferior vena cava, and into the right atrium, or other known access routes as described in the background above. A guidewire GW is advanced via the route and is directed into the right atrium. The guidewire GW traverses the right atrium and traverses through the atrial septum with the aid of a trans-septal needle or a pre-existing hole, thereby entering the left atrium LA. Once the guidewire GW is positioned, the percutaneous entry point and the trans-septal puncture are dilated to permit entry of a guide catheter GC into the left atrium LA. Thereafter, the delivery catheter 220 is advanced over the guidewire GW and through the guide catheter GC into the left atrium LA through the punctured atrial septum and positioned proximate or upstream to the native mitral valve MV. Although described as a transfemoral antegrade approach for percutaneously accessing the mitral valve, the heart valve prosthesis 100 may be positioned within the desired area of the heart via other different entry methods such as a trans-septal antegrade approach via a thoracotomy for accessing the mitral valve. In addition, although described with the use of the guide catheter GC and the guidewire GW, in other embodiments the delivery catheter 220 may access the right atrium without the use of a guidewire and/or a guide catheter.

In FIG. 9, the distal portion of the delivery system 200 is shown positioned in the left atrium LA with the capsule portion 230, including the capsule segment 242 of the outer shaft 222, the capsule segment 248 (obscured from view in FIG. 9 but visible in FIG. 11) of the intermediate shaft 226 (obscured from view in FIG. 9 but visible in FIG. 11), and the distal shaft component 234 of the distal tip component 232 in combination holding the heart valve prosthesis 100 in a radially compressed configuration. With additional reference to FIG. 9, and as will be understood by those knowledgeable in the pertinent art, the handle 244 (not shown in FIGS. 9-13) of the delivery catheter 220, as well as some length of a proximal segment of the delivery catheter 220, are exposed externally of the patient for access by a clinician, even as the heart valve prosthesis 100 has been advanced fully to the desired treatment site (e.g., left atrium LA) in the patient. By manipulating the handle 244 (not shown in FIGS. 9-13) of the delivery catheter 220 from outside the vasculature, a clinician may advance, retract, and remotely manipulate and steer the distal portion of the delivery catheter 220 through the sometimes tortuous intravascular path.

Figure 10:
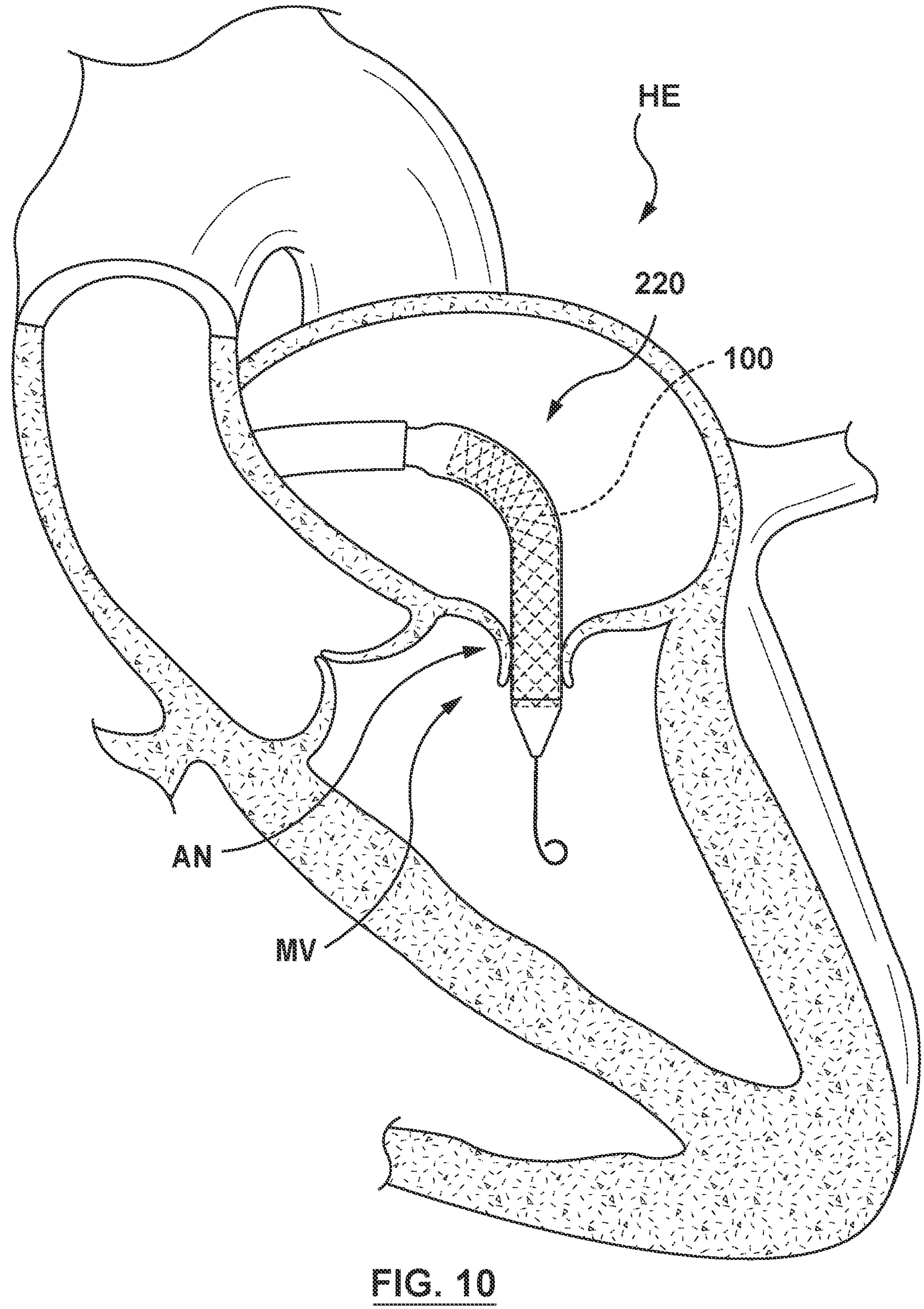
FIG. 10 is an illustration of the delivery system of FIG. 5 in situ, wherein the heart valve prosthesis is shown in the radially compressed configuration and is positioned within an annulus of a native mitral valve.

In a next delivery step shown in FIG. 10, the delivery catheter 220 is advanced into proximity to and/or apposition within the annulus AN and/or leaflets of the native mitral valve MV. The delivery catheter 220 is advanced until the heart valve prosthesis 100 in the radially compressed configuration is centered at the native mitral valve MV.

Figure 11:
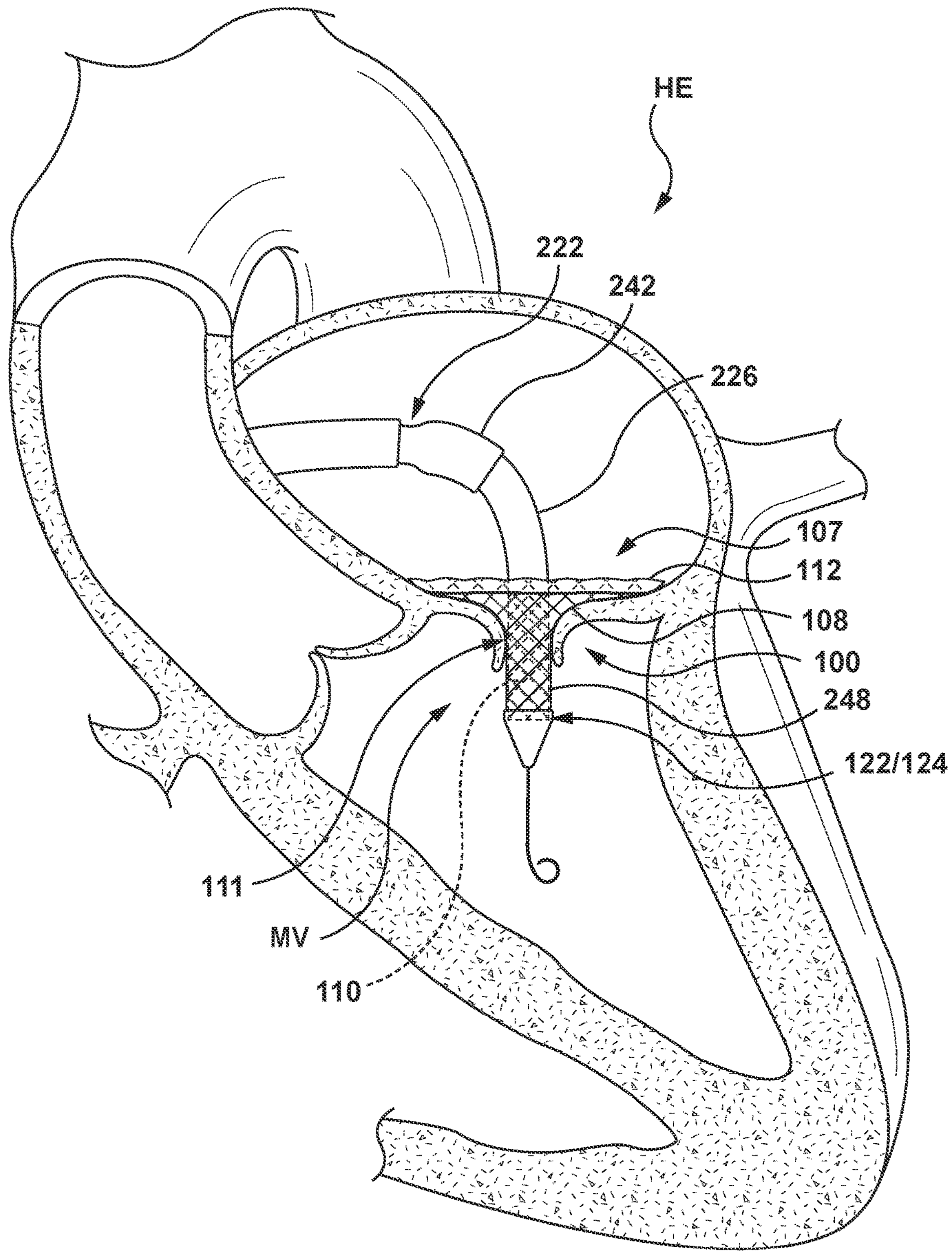
FIG. 11 is an illustration of the delivery system of FIG. 5 in situ with the delivery system in a first stage of deployment.
Figure 11A:
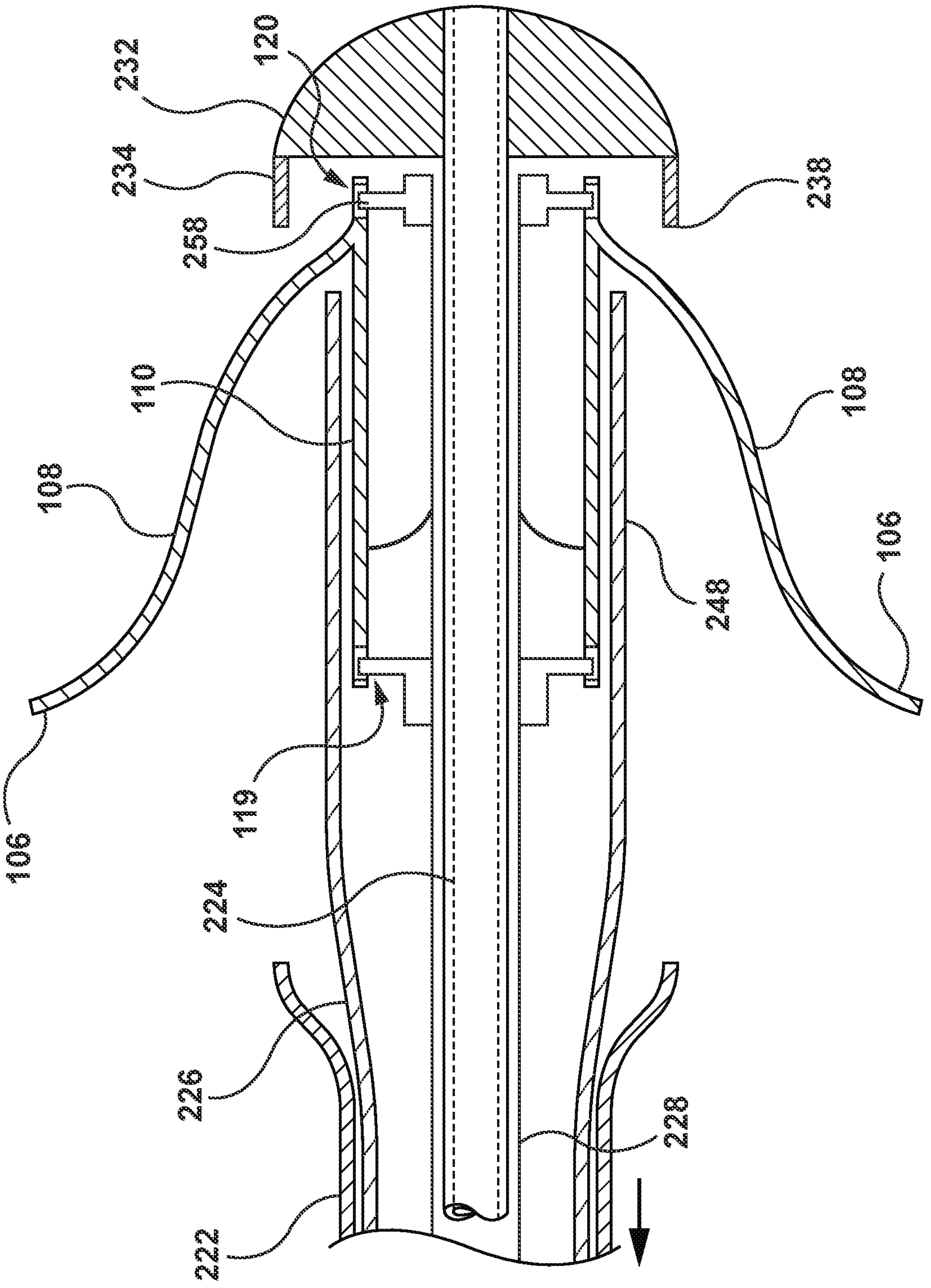
FIG. 11A is a close-up illustration of the delivery system of FIG. 5 in deployment stage of FIG. 11.

Once the delivery catheter 220 is position such that the heart valve prosthesis 100 is positioned within the native mitral valve MV, the first actuator 246 of the handle 244 (not shown in FIGS. 9-13) is actuated to proximally retract the outer shaft 222, as shown in FIGS. 11 and 11A. Proximal retraction of the outer shaft 222 causes the capsule segment 242 of the outer shaft 222 to be proximally retracted such that the capsule segment 242 does not encircle or retain the anchoring member 108 of the heart valve prosthesis 100 (which includes at least the brim 112 of the heart valve prosthesis 100). Proximal retraction of the capsule segment 242 exposes and releases the anchoring member 108 of the heart valve prosthesis 100, thereby enabling at least the brim 112 of the anchoring member 108 to radially expand, as shown in FIG. 11 and FIG. 11A. In addition to radial expansion of the brim 112, the remainder of the anchoring member 108 is also released from the capsule segment 242 and radially expands relative to the inner valve support 110, which remains radially compressed within the capsule segment 248 of the intermediate shaft 226. Retraction of the capsule segment 242 and subsequent deployment of the anchoring member 108 may be considered a first stage of deployment of a deployment process for the heart valve prosthesis 100. After proximal retraction of the capsule segment 242, the capsule segment 248 of the intermediate shaft 226 maintains the inner valve support 110 in the radially compressed state and the distal shaft component 234 of the distal tip component 232 maintains the eyelets 120 in the radially compressed state. If using the delivery catheter 220' of FIGS. 7-8, this first stage of deployment is the same as described above, i.e., retraction of the outer shaft 222' to release the anchoring member 108 and enable at least the brim 112 to radially expand.

With the anchoring member 108 released from the capsule segment 242 of the outer shaft 222, the delivery catheter 220 in some embodiments may be manipulated to properly seat the heart valve prosthesis 100. For example, and not by way of limitation, the delivery catheter 220 may be pushed distally such that the brim 112 of the anchoring member 108 seats against the atrial side of the mitral valve annulus AN. If using the delivery catheter 220' of FIGS. 7-8, this repositioning step is the same as described above.

Figure 12:
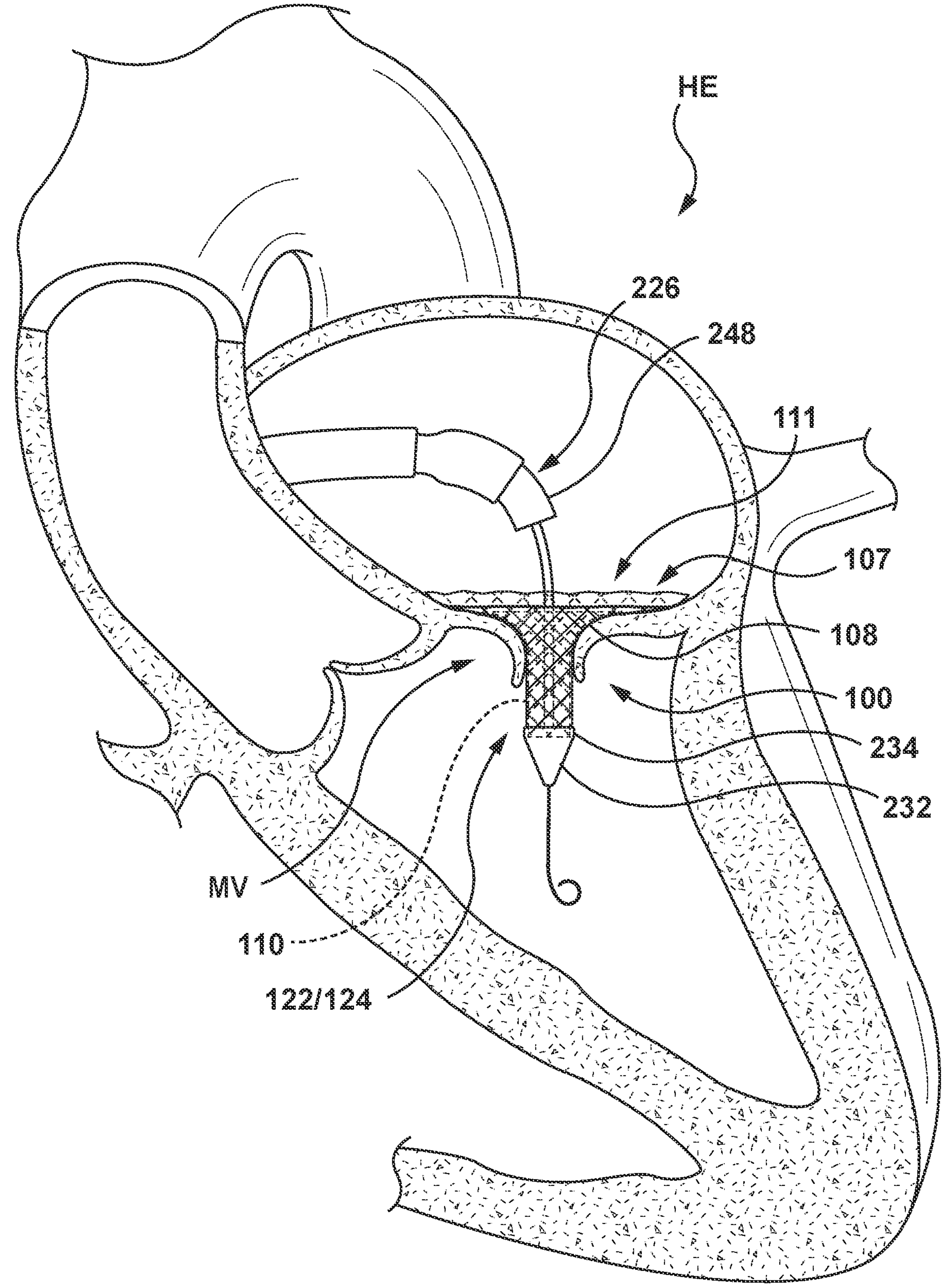
FIG. 12 is an illustration of the delivery system of FIG. 5 in situ with the delivery system in a second stage of deployment.
Figure 12A:
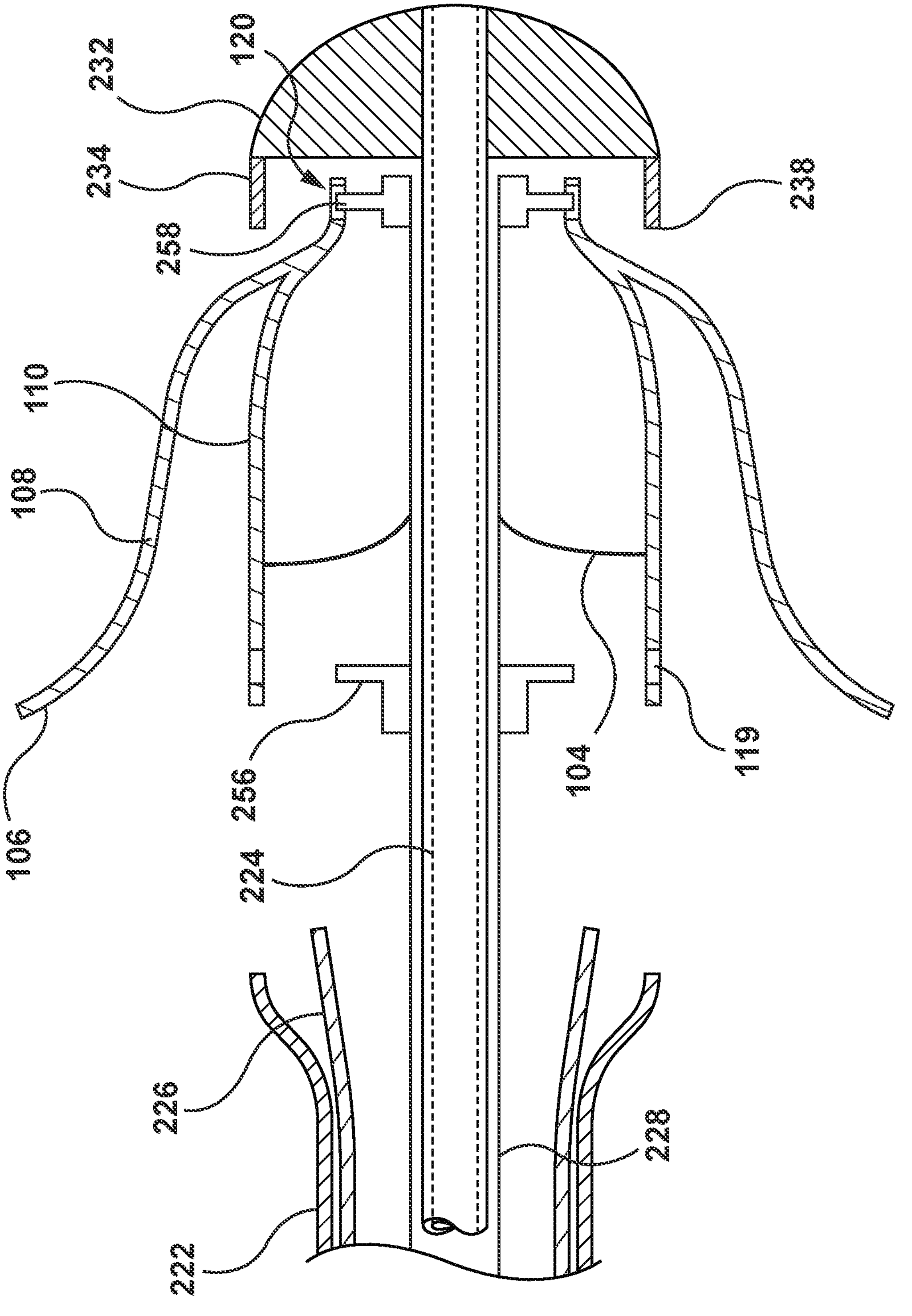
FIG. 12A is a close-up illustration of the delivery system of FIG. 5 in the deployment stage of FIG. 12.

With reference to FIGS. 12 and 12A, once the heart valve prosthesis 100 is properly positioned and the anchoring member 108 has been released from the capsule segment 242, the second actuator 250 of the handle 244 may be actuated to proximally retract the intermediate shaft 226. The intermediate shaft 226 is retracted proximally such that the capsule segment 248 is retracted proximally such that the inner valve support 110 of the heart valve prosthesis 100 is no longer retained within the capsule segment 248. Accordingly, the inner valve support 110 radially expands to the radially expanded state. Retraction of the capsule segment 248 and subsequent deployment of the inner valve support 110 may be considered a second stage of deployment of the deployment process for the heart valve prosthesis 100. After proximal retraction of the capsule segment 248, the distal shaft component 234 of the distal tip component 232 maintains the eyelets 120 in the radially compressed state. If using the delivery catheter 220' of FIGS. 7-8, this second stage of deployment is the same as described above, except that there is no distal shaft component. Thus, using the delivery catheter 220' of FIGS. 7-8, the heart valve prosthesis 100 would be fully deployed upon proximal retraction of the capsule segment 248' of the intermediate shaft 226'.

Figure 13:
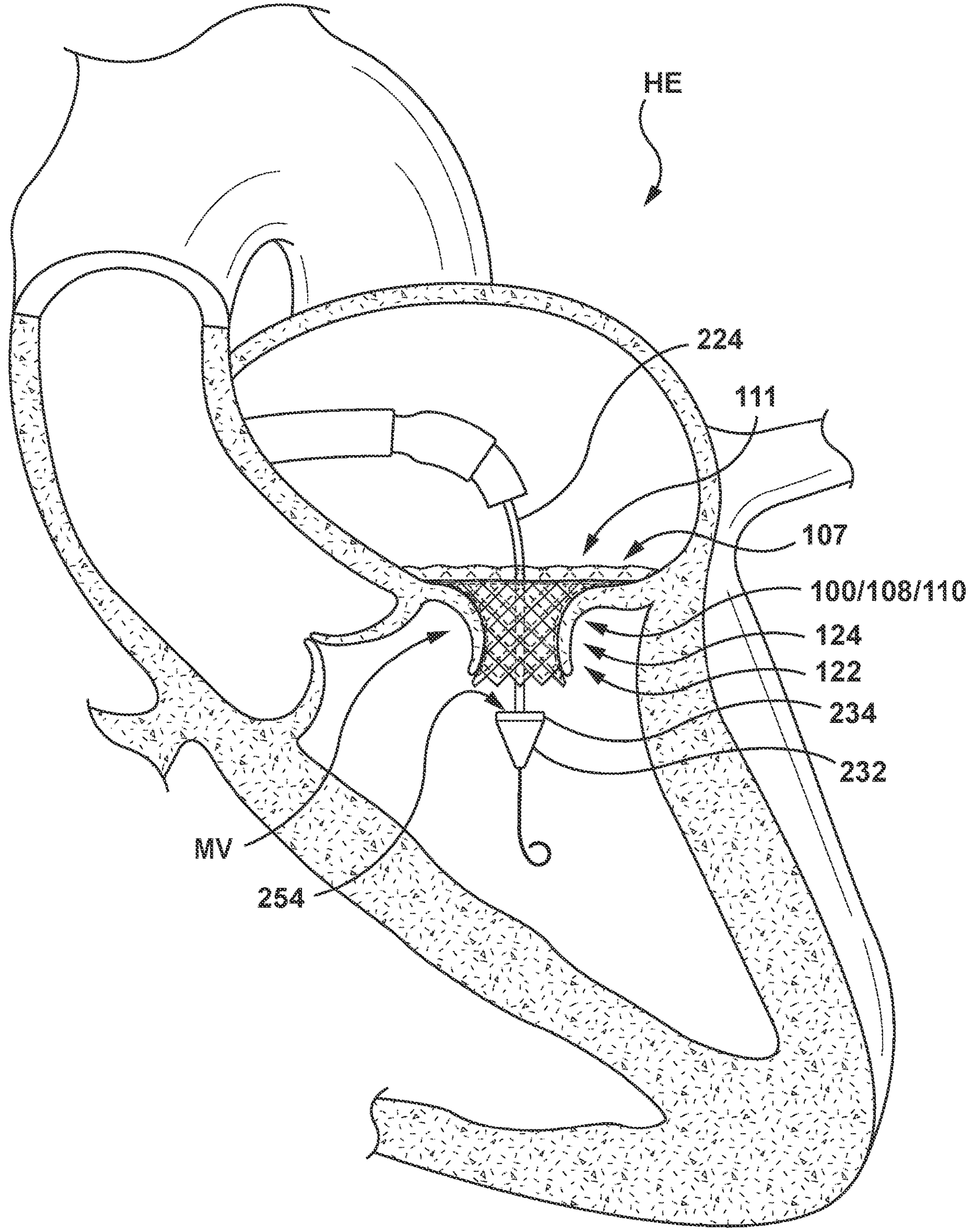
FIG. 13 is an illustration of the delivery system of FIG. 5 in situ with the delivery system in a third stage of deployment.
Figure 13A:
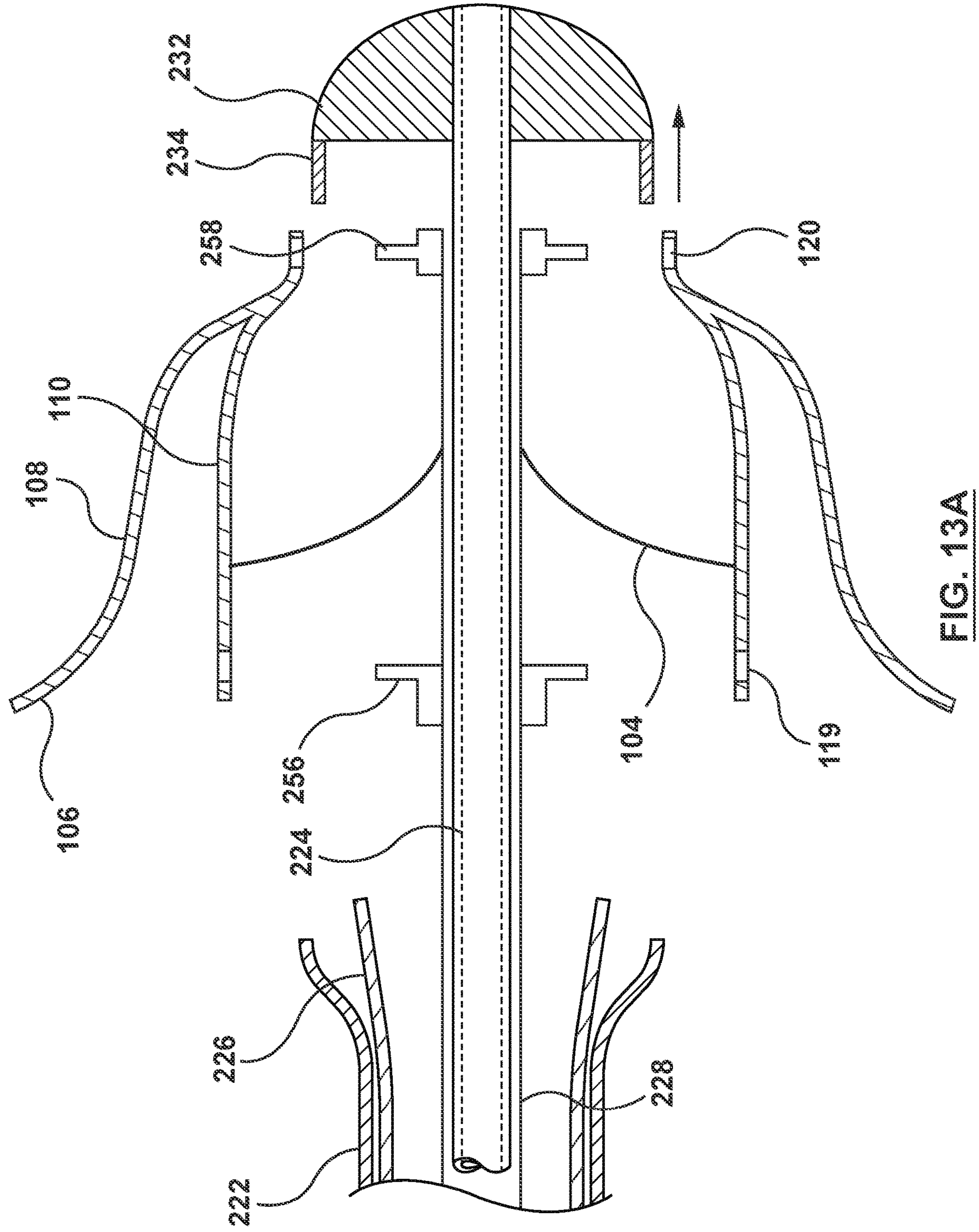
FIG. 13A is a close-up illustration of the delivery system of FIG. 5 in the deployment stage of FIG. 13.

Referring next to FIGS. 13 and 13A, once the anchoring member 108 and the inner valve support 110 are each positioned and deployed within the native mitral valve MV, the third actuator 252 of the handle 244 (not shown in FIGS.

9-13) is actuated such that the inner shaft 224 is advanced in a distal direction. The inner shaft 224 is advanced distally such that the distal shaft component 234 of the distal tip component 232 is also advanced distally to uncover or release the outflow portion 116 of the heart valve prosthesis 100. In the embodiment shown, specifically, the eyelets 120 are released from the recess 254 of the distal shaft component 234. Thus, the distal tip component 232 is distally advanced to expose and release the outflow portion 116 of the heart valve prosthesis 100 and thereby to enable the outflow portion 116 of the heart valve prosthesis 100 to return to a radially expanded state within the native mitral valve MV. Further, release of the outflow portion 116 of the heart valve prosthesis 100 enables complete expansion of the anchoring member 108 and the inner valve support 110 to the radially expanded state. Advancement of the inner shaft 224 and the distal tip component 232 to release the outflow portion of the heart valve prosthesis 100 may be considered a third and final stage of deployment of the deployment process for the heart valve prosthesis 100.

Following delivery, placement and implantation of heart valve prosthesis 100 within the mitral valve MV (or other desired valve location), the delivery catheter 220 of the delivery system 200 is removed from the heart and out of the body of the patient, as would be understood by one of skill in the art.

While the heart valve prosthesis 100 is described in the embodiment of FIGS. 9-13 such that heart valve prosthesis 100 deploys and is fully released from the delivery catheter after the proximal retraction of the capsule segment 242 of the outer shaft 220, the proximal retraction of the capsule segment 248 of the intermediate shaft 226, and the distal advancement of the inner shaft 224 and the distal tip component 232, this is not meant to be limiting. Alternatively, in an embodiment hereof, the first or inflow portion 107 of the anchoring member 108 may be expanded upstream of the desired target location then advanced downstream into the target location before releasing the first or inflow portion 111 of the inner valve support.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of heart valve prosthesis 100 at the target native valve region. In another embodiment, selected outer surfaces of the distal portion of delivery catheter 220 may be treated such that the echogenicity thereof is enhanced. In some embodiments, image guidance components (e.g., IVUS, OCT) may be coupled to delivery catheter 220 to provide three-dimensional images of the vasculature proximate to the target heart valve region to facilitate positioning, orienting and/or deployment of heart valve prosthesis 100 within the heart valve region.

Although FIGS. 9-13 illustrate a mitral valve replacement, the delivery system 200 may be utilized for delivering other valve prostheses for replacement of the respective native valve such as but not limited to an aortic valve.

While the three-stage deployment process is illustrated in FIGS. 9-13, this is not meant to be limiting. As described when describing the three-stage deployment process utilizing the delivery catheter 220, in another embodiment hereof, the delivery catheter 220' may be utilized using a two-stage deployment process to deploy the heart valve prosthesis 100. In the two-stage deployment process utilizing the delivery catheter 220', the anchoring member 108 of heart valve prosthesis 100 is deployed via proximal retraction of the capsule segment 242' of the outer shaft 222'. Next, the inner valve support 110 is deployed via proximal retraction of the capsule segment 248' of the intermediate shaft 226'.

In a further embodiment hereof, the outflow portion 116 of the heart valve prosthesis 100 retained by the distal shaft component 234 may be released prior to retraction of the capsule segment 242 of the outer shaft 222 and/or retraction of the capsule segment 248 of the intermediate shaft 226. Thus, the order or sequence of the multi-stage deployment is not limited to the sequence described above, although the sequence described above is the preferred sequence.

While various embodiments according to the present invention have been described above, it should be understood that they have been presented by way of illustration and example only, and not limitation. Various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of delivering and deploying a heart valve prosthesis, the method comprising:

positioning a delivery catheter at a site of a native heart valve with the heart valve prosthesis in a radially compressed configuration within the delivery catheter, wherein the heart valve prosthesis includes an outer member coupled to an inner member and a prosthetic valve coupled to the inner member, wherein the delivery catheter includes an outer shaft, an intermediate shaft, and an inner shaft;

retracting the outer shaft to release the outer member of the heart valve prosthesis from the outer shaft such that the outer member radially expands;

after the step of retracting the outer shaft, advancing the delivery catheter such that a brim of the outer member engages an upstream side of an annulus of the native heart valve; and after the step of advancing the delivery catheter, retracting the intermediate shaft to release the inner member of the heart valve prosthesis from the intermediate shaft such that the inner member radially expands.

2. The method of claim 1, wherein the native heart valve is an atrioventricular valve, and wherein the brim engages the atrial side of the annulus of the native heart valve.

3. The method of claim 2, wherein the native heart valve is a mitral valve.

4. The method of claim 3, wherein positioning the delivery catheter at the site of a native heart valve comprises advancing the delivery catheter from a right atrium to a left atrium via a puncture in a septal wall.

5. The method of claim 2, wherein the native heart valve is a tricuspid valve.

6. The method of claim 1, wherein an inflow portion of the heart valve prosthesis faces a proximal portion of the delivery catheter.

7. The method of claim 1, wherein the delivery catheter further includes a distal tip component coupled to a distal portion of the inner shaft, the distal tip component including a distal shaft component extending proximally from the distal tip component, wherein in the delivery configuration the distal shaft component encircles an outflow portion of the heart valve prosthesis, further comprising:

after the step of retracting the intermediate shaft, distally advancing the inner shaft to distally advance the distal shaft component to release the outflow portion of the heart valve prosthesis from the distal shaft component such that the outflow portion of the heart valve prosthesis radially expands.

8. A method of delivering and deploying a heart valve prosthesis, the method comprising:

positioning a delivery catheter at a site of a native heart valve with the heart valve prosthesis in a radially compressed configuration within the delivery catheter, wherein the heart valve prosthesis includes an outer member coupled to an inner member and a prosthetic valve coupled to the inner member, wherein the delivery catheter includes an outer shaft, an intermediate shaft, an inner shaft, and a distal tip component coupled to a distal portion of the inner shaft, the distal tip component including a distal shaft component extending proximally from the distal tip component, wherein in the delivery configuration the distal shaft component encircles an outflow portion of the heart valve prosthesis;

retracting the outer shaft to release the outer member of the heart valve prosthesis from the outer shaft such that the outer member radially expands;

retracting the intermediate shaft to release the inner member of the heart valve prosthesis from the intermediate shaft such that the inner member radially expands; and advancing the inner shaft to distally advance the distal shaft component to release the outflow portion of the heart valve prosthesis from the distal shaft component such that the outflow portion of the heart valve prosthesis radially expands.

9. The method of claim 8, further comprising, after the step of retracting the outer shaft, advancing the delivery catheter such that a brim of the outer member engages and upstream side of an annulus of the native heart valve.

10. The method of claim 9, wherein the native heart valve is an atrioventricular valve, and wherein the brim engages the atrial side of the annulus of the native heart valve.

11. The method of claim 10, wherein the native heart valve is a mitral valve.

12. The method of claim 11, wherein positioning the delivery catheter at the site of a native heart valve comprises advancing the delivery catheter from a right atrium to a left atrium via a puncture in a septal wall.

13. The method of claim 10, wherein the native heart valve is a tricuspid valve.

* * * * *